(12) United States Patent
Kumpalume et al.

(10) Patent No.: US 9,809,558 B2
(45) Date of Patent: Nov. 7, 2017

(54) COMPOUNDS FOR AFFINITY CHROMATOGRAPHY AND FOR EXTENDING THE HALF-LIFE OF A THERAPEUTIC AGENT

(71) Applicant: GLAXOSMITHKLINE INTELLECTUAL PROPERTY DEVELOPMENT LIMITED, Middlesex (GB)

(72) Inventors: Peter Kumpalume, Stevenage (GB); Oliver Schon, Stevenage (GB); Christine Patricia Donahue, Waltham, MA (US); Ghotas Evindar, Waltham, MA (US); David I. Israel, Waltham, MA (US); David Paolella, King of Prussia, PA (US); Letian Kuai, Waltham, MA (US); Ninad V. Prabhu, Waltham, MA (US)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 15/026,725

(22) PCT Filed: Oct. 1, 2014

(86) PCT No.: PCT/IB2014/064998
§ 371 (c)(1),
(2) Date: Apr. 1, 2016

(87) PCT Pub. No.: WO2015/049651
PCT Pub. Date: Apr. 9, 2015

(65) Prior Publication Data
US 2016/0221962 A1 Aug. 4, 2016

Related U.S. Application Data

(60) Provisional application No. 61/885,146, filed on Oct. 1, 2013, provisional application No. 62/025,994, filed on Jul. 17, 2014.

(51) Int. Cl.
| | | |
|---|---|---|
| *C07D 235/18* | (2006.01) |
| *A61K 31/4184* | (2006.01) |
| *C07D 401/06* | (2006.01) |
| *C07D 401/10* | (2006.01) |
| *C07D 235/24* | (2006.01) |
| *C07D 417/14* | (2006.01) |
| *A61K 31/454* | (2006.01) |
| *A61K 31/4545* | (2006.01) |
| *C07D 411/14* | (2006.01) |

(52) U.S. Cl.
CPC ........ *C07D 235/18* (2013.01); *A61K 31/4184* (2013.01); *A61K 31/454* (2013.01); *A61K 31/4545* (2013.01); *C07D 235/24* (2013.01); *C07D 401/06* (2013.01); *C07D 401/10* (2013.01); *C07D 411/14* (2013.01); *C07D 417/14* (2013.01)

(58) Field of Classification Search
CPC .. C07D 235/18; C07D 235/24; C07D 401/06; C07D 401/10; C07D 411/14; C07D 417/14; A61K 31/4184; A61K 31/454; A61K 31/4545
USPC ........................................................ 514/316
See application file for complete search history.

(56) References Cited

U.S. PATENT DOCUMENTS

| 7,112,600 B1 | 9/2006 | Hashimoto et al. |
| 7,220,769 B2 * | 5/2007 | Farina .................. C07D 235/02 514/393 |
| 7,777,051 B2 | 8/2010 | Wang et al. |
| 2008/0207635 A1 | 8/2008 | Anikin et al. |

FOREIGN PATENT DOCUMENTS

| SG | 11201503603 U | 3/2013 |
| WO | WO 2004/012736 A1 | 2/2004 |
| WO | WO 2012/017021 A2 | 2/2012 |
| WO | WO 2012/020080 A2 | 2/2012 |
| WO | 2014086739 A1 | 6/2014 |

OTHER PUBLICATIONS

Dasari, et al., "Hoechst-IR: An Imaging Agent That Detects Necrotic Tissue in Vivo by Binding Extracellular DNA", *Organic Letters*, vol. 12, No. 15, pp. 3300-3303 (2010).
El-Nezhawy, et al., "Synthesis and analgesic activity of (2,3-diphenyl-1H-indol-5-YL)piperazin-1-yl methanone derivatives", *Pharmaceutical Chemistry Journal*, vol. 43, No. 1, pp. 25-29 (2009).
Frischkorn, et al., "Naphthylendi(heteroarene), III. Synthese und spektroskopisches Verhalten von 2,2'-Naphthylendibenzazolen" *Liebigs Annalen Der Chemie*, vol. 1984, No. 6, pp. 1129-1136 (1984).
Hoen, et al., "Selective Inhibition of an Apicoplastic Aminoacyl-tRNA Synthetase from Plasmodium falciparum", *Chembiochem*, vol. 14, No. 4, pp. 499-509 (2013).
Pollaro, et al., "Strategies to prolong the plasma residence time of peptide drugs", *Medchemcomm, Royal Society of Chemistry*, United Kingdom, vol. 1, No. 5, pp. 319-324 (2010).

(Continued)

*Primary Examiner* — Yevegeny Valenrod
(74) *Attorney, Agent, or Firm* — James J. Kang; Andrea V. Lockenour

(57) ABSTRACT

Compounds useful for affinity chromatography as presented, more particularly for use in affinity chromatography to purify serum albumin, especially human serum albumin (HSA) and fusion proteins thereof. Methods for extending the half-life of therapeutic agents are also presented, particularly therapeutic peptide agents and small molecules, such as by conjugation of compounds described herein to the therapeutic peptide or small molecule, which upon administration, binds to HSA, thereby providing a prolonged release of the therapeutic agent.

32 Claims, 5 Drawing Sheets

(56) References Cited

OTHER PUBLICATIONS

Sando, et al., "Transcription monitoring using fused RNA with a dye-binding light-up aptamer as a tag: a blue fluorescent RNA", *Chemical Communications*, No. 33, p. 3858 (2008).
Behrens et al., Synthesis of a Hoechst 32258 analogue amino acid building block for direct incorporation of a fluorescent, high-affinity DNA binding motif into peptides. Bioconjug Chem. Nov.-Dec. 2001;12(6):1021-7.

* cited by examiner

COMPOUNDS FOR AFFINITY CHROMATOGRAPHY AND FOR EXTENDING THE HALF-LIFE OF A THERAPEUTIC AGENT

This application is a 371 of International Application No. PCT/IB2014/064998, filed Oct. 1, 2014, which claims the benefit of U.S. Provisional Application Nos. 61/885,146 filed on Oct. 1, 2013 and U.S. 62/025,994 filed on Jul. 17, 2014, which are incorporated herein in their entireties.

FIELD OF THE INVENTION

The present invention relates to compounds for use in affinity chromatography, more particularly to compounds for use in affinity purification of serum albumin, especially human serum albumin (HSA). The compounds are also useful for extending the half-life of therapeutic agents, particularly therapeutic peptide agents and small molecules, such as by conjugation to the therapeutic peptide or small molecule, which, upon administration, binds to HSA, thereby providing a prolonged release of the therapeutic agent.

BACKGROUND ART

Small molecules which bind to human serum albumin have been described for use in purifying biomolecules such as serum albumins including human serum albumin (HSA), antibodies and fusion proteins (see S. Subramanian, Dye-Ligand Affinity Chromatography: The Interaction of Cibacron Blue F3GA® With Proteins and Enzymes, *CRC Critical Reviews in Biochemistry* (1984) vol 16 (2), pp. 169 —205; U.S. Pat. No. 4,722,896; U.S. Pat. No. 5,849,874; and PCT Publication No. WO 2012/020080 A2). Similarly, small molecules which bind to human serum albumin have been described which are useful in prolonging the half-life of therapeutic agents which have been administered by injection, particularly therapeutic peptide agents (see e.g. L. Pollaro and C. Heinis, Strategoes to Prolong the Plasma Residence Time of Peptide Drugs, *Med. Chem. Commun.* (2010) 1, 319-324).

There is a need for additional improved compounds which can be used to purify, separate and/or capture such biomolecules away from other biomolecules and compounds present in cell lysates or other liquid mixtures and solutions. Likewise, there is a need for additional compounds which can be used to safely and effectively increase the half-life of existing therapeutic molecules, particularly therapeutic peptides, polypeptides and small molecules, which when administered to a subject enter the subject's circulation.

SUMMARY OF THE INVENTION

Embodiments of the present invention feature novel compounds that are useful as affinity agents for directly purifying a variety of biomolecules, such as plasma proteins, including serum albumins, particularly human serum albumin and HSA-fusion proteins. Other biomolecules that may be purified include immunoglobulins, fibrinogen, α1-acid glycoproteins, etc; enzymes, including amylases, cellulases, calf-intestinal alkaline phosphatase (CIAP), lactate dehydrogenase (LDH), etc.; and artificial proteins or protein domains, including affinity tagged proteins or domains (such as with 6His, FLAG, GST, etc.), Fc-fusion proteins, domain antibodies, etc. In addition, such compounds, when conjugated to a therapeutic agent particularly a peptide therapeutic agent, are useful in extending the half-life of that therapeutic agent in the blood, upon administration. Embodiments of the invention provide novel chemotypes that have high affinity and specificity to HSA, including its fragments and variants, such as when coupled to agarose or another substrate. Moreover, the affinity resin technology has significantly greater selectivity than commercially available ligands for the purification of HSA and HSA-fusion proteins. The greater selectivity is achieved through specific interaction of the compounds of the invention with a binding site on albumin.

Embodiments of the invention are compounds of formula I

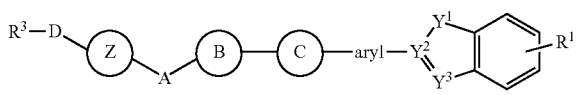

or formula II

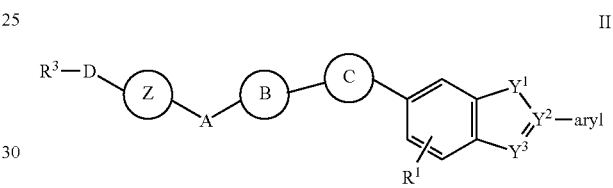

or a salt thereof, wherein $R^1$ is H, —Cl, —F, —Br, —I, —OH, —CN, —NO$_2$, substituted or unsubstituted $C_1$-$C_6$ alkyl, substituted or unsubstituted $C_1$-$C_6$ alkenyl, substituted or unsubstituted cycloalkyl, aryl or heteroaryl;

$R^3$ is —[(CH$_2$)$_2$E]$_n$(CH$_2$)$_2$NR'R" and n is any integer from 0 through 30, wherein R' and R" are each independently H, substituted or unsubstituted $C_1$-$C_6$ alkyl, substituted or unsubstituted $C_1$-$C_6$ alkenyl, or substituted or unsubstituted cycloalkyl;

aryl is any substituted or unsubstituted fully or partially aromatic hydrocarbon substituent or heteroaryl substituent;

$Y^1$ and $Y^3$ are independently C, O, N, NR$^2$ or S, wherein $R^2$ is H, substituted or unsubstituted $C_1$-$C_6$ alkyl, substituted or unsubstituted $C_1$-$C_6$ alkenyl, substituted or unsubstituted cycloalkyl, aryl or heteroaryl; $Y^2$ is C or N;

A and D are independently

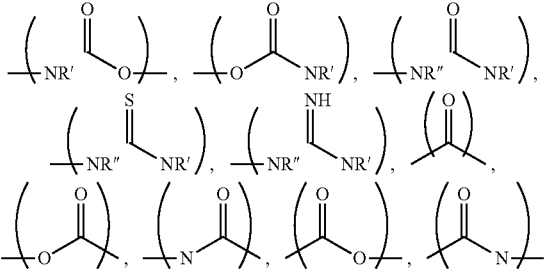

amidine, thioamide or A and/or D is absent, wherein R' is H, substituted or unsubstituted $C_1$-$C_6$ alkyl, substituted or unsubstituted $C_1$-$C_6$ alkenyl, substituted or unsubstituted cycloalkyl, aryl or heteroaryl;

B is substituted or unsubstituted $C_4$-$C_9$-cycloalkyl, substituted or unsubstituted $C_4$-$C_9$-heterocycloalkyl comprising N, O or S, substituted or unsubstituted heteroaryl comprising N, O, S or B is absent;

C is any of

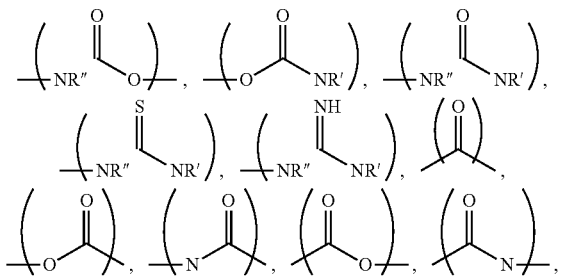

aryl, heteroaryl, amidine, thioamide or C is absent, wherein R' and/or R" are each independently H, substituted or unsubstituted $C_1$-$C_6$ alkyl, substituted or unsubstituted $C_1$-$C_6$ alkenyl, substituted or unsubstituted cycloalkyl, aryl or heteroaryl;

E is $CH_2$, O, NH or S, or E is absent;

Z is substituted or unsubstituted aryl, substituted or unsubstituted heteroalkyl comprising N, O or S, or substituted or unsubstituted heteroaryl comprising N, O, S or Z is absent.

In another aspect, the invention provides compounds of formula III

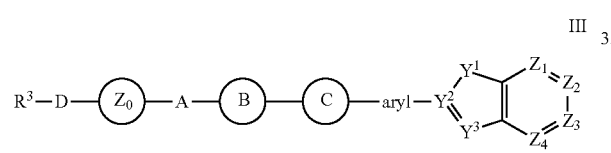

or formula IV

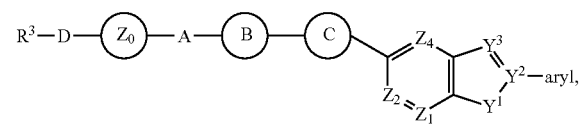

or a salt thereof, wherein:

each $Z_1$, $Z_2$, $Z_3$, and $Z_4$ is independently selected from N and $CR^1$ and no more than two of $Z_1$, $Z_2$, $Z_3$, and $Z_4$ are N, and each $R^1$ is independently selected from H, —Cl, —F, —Br, —I, —OH, —CN, —$NO_2$, substituted or unsubstituted $C_1$-$C_6$ alkyl, substituted or unsubstituted $C_1$-$C_6$ alkoxyl, substituted or unsubstituted $C_1$-$C_6$ alkenyl, substituted or unsubstituted cycloalkyl, aryl or heteroaryl;

$R^3$ is —$[(CH_2)_2E]_n(CH_2)_2NR'R''$ and n is any integer from 0 through 30, wherein R' and R" are each independently H, substituted or unsubstituted $C_1$-$C_6$ alkyl, substituted or unsubstituted $C_1$-$C_6$ alkenyl, or substituted or unsubstituted cycloalkyl;

aryl is any substituted or unsubstituted fully or partially aromatic hydrocarbon substituent or heteroaryl substituent;

$Y^1$ and $Y^3$ are independently C, $CR^2$, O, N, $NR^2$ or S, wherein $R^2$ is H, substituted or unsubstituted $C_1$-$C_6$ alkyl, substituted or unsubstituted $C_1$-$C_6$ alkenyl, substituted or unsubstituted cycloalkyl, aryl or heteroaryl;

$Y^2$ is C;

A and D are independently

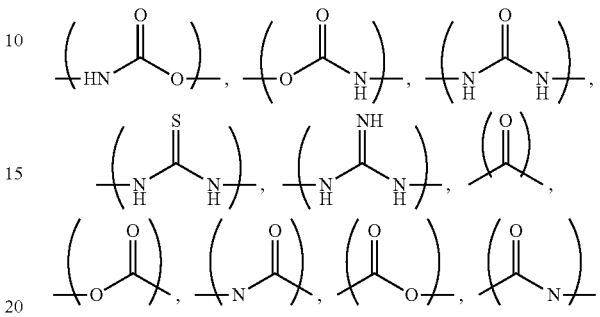

amidine, thioamide or A and/or D is absent;

B is substituted or unsubstituted $C_4$-$C_9$-cycloalkyl, substituted or unsubstituted $C_4$-$C_9$-heterocycloalkyl comprising N, O or S, substituted or unsubstituted heteroaryl comprising N, O, S or B is absent;

C is any of

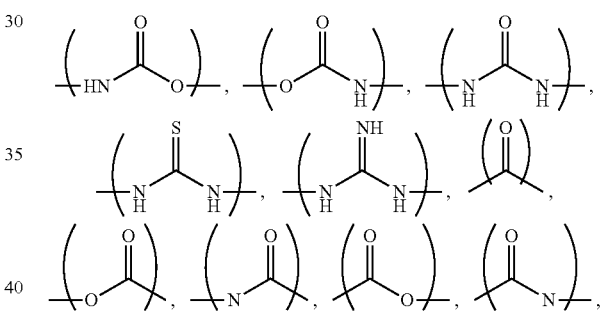

aryl, heteroaryl, amidine, thioamide;

E is $CH_2$, O, NH or S, or E is absent; and

Z is substituted or unsubstituted aryl, substituted or unsubstituted heteroalkyl comprising N, O or S, or substituted or unsubstituted heteroaryl comprising N, O, S, or Z is absent.

As disclosed herein, compounds of formula I, formula II, formula III and formula IV may be bound to a solid phase to prepare an affinity chromatography solid phase, which is useful for separation of a protein of interest from an aqueous solution comprising the protein and one or more impurities. For example, the solid phase is agarose. The protein of interest may comprise, for example, human serum albumin. The aqueous solution may be: from a cell lysate, from a cell harvest/broth, isolated from a bodily fluid, for example blood, or from other mixtures. For example, affinity agarose material as disclosed herein may be used to purify, separate or capture a variety of biomolecules from cell lysates and other mixtures. Biomolecules that may be purified, separated or captured from other biomolecules and impurities in liquid/aqueous solution mixtures are biomolecules such as plasma proteins including serum albumins immunoglobulins, fibrinogen, α1-acid glycoproteins, etc; enzymes including amylases, cellulases, calf-intestinal alkaline phosphatase (CIAP), lactate dehydrogenase (LDH), etc.; and artificial proteins or protein domains including affinity tagged proteins or domains (such as with 6His, FLAG, GST, etc.), HSA-fusion proteins, Fc-fusion proteins, domain antibodies, etc.

Compounds as described herein may also be used to extend the half-life of therapeutic agents, particularly peptide, polypeptide and small molecule therapeutic agents. Typically peptides are cleared from the bloodstream within minutes after intravenous administration. The kidneys appear to completely filter out molecules below 5 kDa, while larger peptides (above ~50-70 kDa) appear to be efficiently retained and circulated. However, it is known that renal clearance of some peptides can be reduced through binding to accessible membrane proteins or serum proteins. The life-time of molecules in the circulation is generally expressed as plasma half-life, defined as the time it takes for the concentration of molecules in circulation to be reduced by half through elimination by the system (kidneys, etc.). Because elimination from the blood of molecules administered intravenously is nearly always a biphasic process (the first phase is rapid decline because of distribution to peripheral tissue), the second phase (reduction through elimination by kidneys etc.) is the part of the reduction associated with the term "plasma half-life", also commonly referred to as "elimination half-life."

Embodiments of the invention thus provide compounds of formula I or formula II as described herein, conjugated to a therapeutic agent, particularly a peptide or polypeptide therapeutic agent, for use in extending the elimination half-life or plasma half-life of the therapeutic agent in the blood stream.

BRIEF DESCRIPTIONS OF THE DRAWINGS

The foregoing features of the invention will be more readily understood by reference to the following detailed description, taken with reference to the accompanying drawings, in which:

FIG. 4b shows a graphic representation of the results from FIG. 4a.

DETAILED DESCRIPTION OF SPECIFIC EMBODIMENTS

Figure 1:
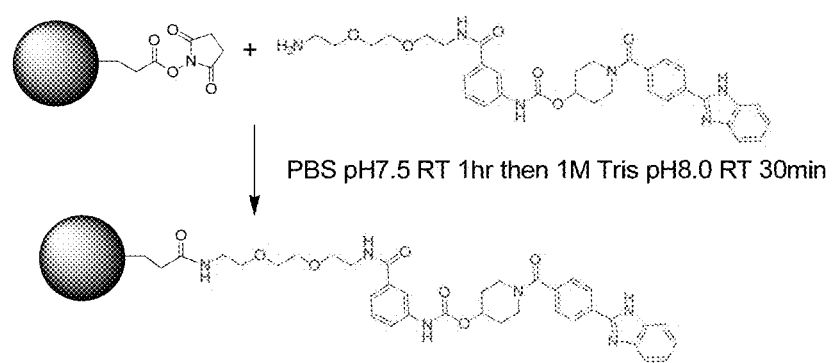
FIG. 1 shows a schematic of a reaction between activated agarose and compounds as described herein to prepare affinity-conjugated agarose beads.

Definitions. As used in this description and the accompanying claims, the following terms shall have the meanings indicated, unless the context otherwise requires:

DIPEA means N,N-diisopropylethylamine and is also referred to as Hunig's base

DMF means dimethylformamide

EDTA means N,N-Ethylenediamine-N,N,N',N'-tetraacetic acid

HATU means 1-[Bis(dimethylamino)methylene]-1H-1,2,3-triazolo[4,5-b]pyridinium 3-oxid hexafluorophosphate h means hour(s)

HSA means human serum albumin

Mimetic Blue® means Mimetic Blue® SA HL P6XL from ProMetic BioSciences Ltd as described in (www.prometicbiosciences.com/assets/files/app_notes/Mimetic %20Blue %20SA % 20HL %20P6XL %20Appliation %20Note %20-%20Albumin-fusion %20protein %20protein %20(091110)%20v2[1].pdf), Mimetic Blue® SA HL min means minute(s)

MSA means mouse serum albumin

NP40 means the detergent Tergitol-type NP-40, also known as nonyl phenoxypolyethoxylethanol OD means optimal density, as measured using a spectrophotometer $OD_{280}$ means optimal density as measured using a spectrophotometer at 280 nm PBS means phosphate buffered saline Pierce NHS-activated agarose means N-hydroxysuccinimide-activated agarose, such as from Thermo Scientific P6XL (Product Cod 3125), Application Note—Capture and purification of recombinant albumin-fusion protein using Mimetic Blue® SA HL P6XL.

rpm mean revolutions per minute

RT or rt means room temperature

RSA means rat serum albumin

SDS means sodium dodecyl sulfate

TFA means trifluoroacetic acid

As described herein, "alkyl" means any aliphatic hydrocarbon substituent that is a straight-chain or branched chain or cyclic hydrocarbon or combination thereof, which is fully saturated. As used herein, alkyl may also refer to a hydrocarbon that is mono- or polyunsaturated, or a combination thereof. Examples of saturated hydrocarbon substituents include, but are not limited to the substituents known as methyl, ethyl, n-propyl, isopropyl, n-butyl, t-butyl, isobutyl, sec-butyl, cyclohexyl, substituted cyclohexyl, homologs and positional and stereoisomers of, e.g. substituted or unsubstituted pentyl, hexyl, heptyl, octyl substituents and the like. An alkyl substituent, as used herein, includes alkyl substituents which may have one or more double or triple bonds.

As described herein, "amino alkyl" means an alkyl substituent that has one or more hydrogens in the hydrocarbon substituted with an amino substituent, e.g. —NH$_2$, —NHR, —NR$_2$, —N=R, =NR and the like.

As described herein, "substituted or unsubstituted amino alkyl" means that an amino alkyl substituent may be —NH$_2$ (unsubstituted) or have one or more of the hydrogen atoms in the amino group substituted with a carbon substituent, as described by —NHR, —N=R, =NR and the like (substituted).

As described herein, "aryl" means any aromatic hydrocarbon substituent such as benzene, naphthalene, phenanthrene, pyrene, benzo[a]anthracene, benzo[a]pyrene etc, e.g. phenyl, naphthyl, phenanthryl, etc. As used herein, aryl also includes heteroaryl", including any fully or partially aromatic heterocyclic substituent. Examples include, but are not limited to, pyrrole, pyridine, pyrimidine, purine, pyran, furan, thiophene, thiazole, indole, imidazole, thioimidazole, oxazole, azepine, thiopene, thiazapine, quinoline, oxepine, oxadiazole substituents.

As described herein "substituted or unsubstituted aryl" means any aryl substituent that has no substituent other than hydrogen on the aromatic ring (phenyl, naphthyl, phenanthryl etc.) or an aryl substituent where one or more hydrogens is substituted with a substituent such as carbon (alkyl etc.), amine (amino, aminoalkyl, imino, nitro, nitroalkyl, etc.), sulfur (thio, thioalkyl, sulfonate, sulfate, etc.), oxo (carbonyl, aldehyde, acid, ester, ether, etc.), halogen (chloro, fluoro, bromo, iodo) group etc. Examples include but are not limited to benzyl substituents, and toluene, phenol, aniline, benzonitrile, acetophenone, benzaldehyde, benzoic acid, xylene, and nitrobenzene substituents, As described herein, "substituted or unsubstituted heteroaryl" means any heteroaryl substituent, as described above, wherein one or more hydrogens on the ring carbons is substituted with N, O or S.

Embodiments of the invention provide compounds of formula I

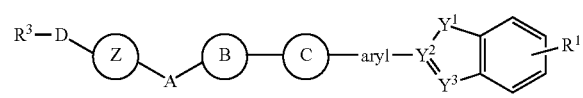

or a salt thereof, wherein: $R^1$ is H, —Cl, —F, —Br, —I, —OH, —CN, —NO$_2$, substituted or unsubstituted $C_1$-$C_6$ alkyl, substituted or unsubstituted $C_1$-$C_6$ alkenyl, substituted or unsubstituted cycloalkyl, aryl or heteroaryl;

$R^3$ is —[(CH$_2$)$_2$E]$_n$(CH$_2$)$_2$NR'R" and n is any integer from 0 through 30, wherein R' and R" are each independently H, substituted or unsubstituted $C_1$-$C_6$ alkyl, substituted or unsubstituted $C_1$-$C_6$ alkenyl, or substituted or unsubstituted cycloalkyl; aryl is any substituted or unsubstituted fully or partially aromatic hydrocarbon substituent or heteroaryl substituent;

$Y^1$ and $Y^3$ are independently C, O, N, NR$^2$ or S, wherein $R^2$ is H, substituted or unsubstituted $C_1$-$C_6$ alkyl, substituted or unsubstituted $C_1$-$C_6$ alkenyl, substituted or unsubstituted cycloalkyl, aryl or heteroaryl;

$Y^2$ is C or N;

A and D are independently

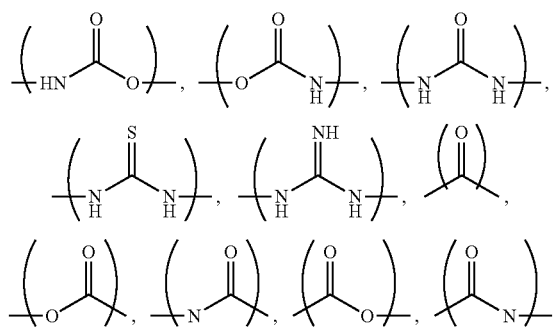

amidine, thioamide or A and/or D is absent;

B is substituted or unsubstituted $C_4$-$C_9$-cycloalkyl, substituted or unsubstituted $C_4$-$C_9$-heterocycloalkyl comprising N, O or S, substituted or unsubstituted heteroaryl comprising N, O, S or B is absent;

C is any of

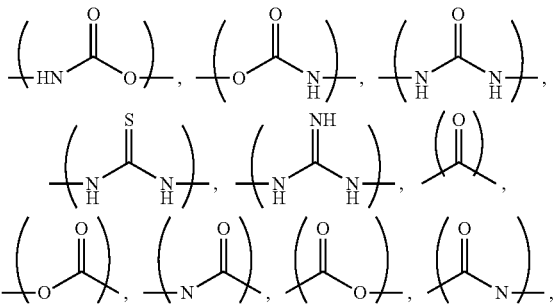

aryl, heteroaryl, amidine, thioamide;

E is CH$_2$, O, NH or S, or E is absent;

Z is substituted or unsubstituted aryl, substituted or unsubstituted heteroalkyl comprising N, O or S, or substituted or unsubstituted heteroaryl comprising N, O, S or is Z is absent;

Related embodiments provide compounds of formula I, wherein $R^1$ is H, —Cl, —F, —Br or —I; $R^3$ is —[(CH$_2$)$_2$E]$_n$(CH$_2$)$_2$NR'R" and n is any integer from 0 through 12, wherein R' and R" are each independently H, —CH$_3$, —CH$_2$CH$_3$, —CH(CH$_3$)$_2$, —CH$_2$CH(CH$_3$)$_2$, —(CH)$_n$CH$_3$ wherein n is 1, 2, 3, 4 or 5, or —C(CH$_3$)$_3$; aryl is a substituted or unsubstituted phenyl, tolyl, xylyl, naphthyl, benzyl, thienyl, indolyl, pyrrolyl, pyridinyl, pyrimidinyl, purinyl, pyranyl, furanyl, thiophenyl, thiazolyl, imidazolyl, thioimidazolyl, oxazolyl, azepinyl, thiopenyl, thiazapinyl, quinolinyl, oxepinyl or oxadiazolyl group;

$Y^1$ and $Y^3$ are independently C, O, N, NR$^2$ or S, wherein $R^2$ is H, —CH$_3$, —CH$_2$CH$_3$, —CH(CH$_3$)$_2$, —CH$_2$CH(CH$_3$)$_2$, —(CH)$_n$CH$_3$ wherein n is 1, 2, 3, 4 or 5, or —C(CH$_3$)$_3$;

$Y^2$ is C or N;

A and D are independently

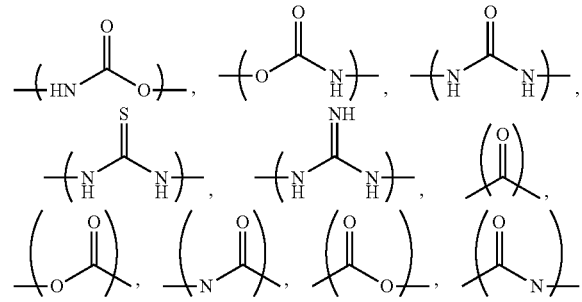

amidine, thioamide or A and/or D is absent; B is substituted or unsubstituted $C_4$-$C_9$-cycloalkyl, substituted or unsubstituted $C_4$-$C_9$-heterocycloalkyl comprising N, substituted or unsubstituted heteroaryl comprising N, S or O or B is absent; C is any of

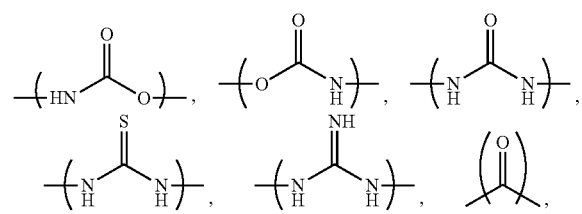

-continued

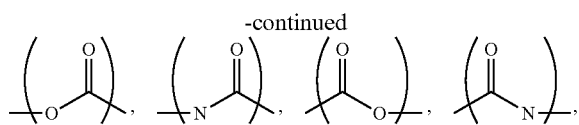

aryl, heteroaryl, amidine, thioamide or C is absent; E is CH$_2$, O, NH or S, or E is absent; Z is substituted or unsubstituted aryl or substituted or unsubstituted heteroaryl comprising N, O or S, or Z is absent; or a salt thereof.

Certain embodiments of the invention provide compounds of formula Ia as shown below,

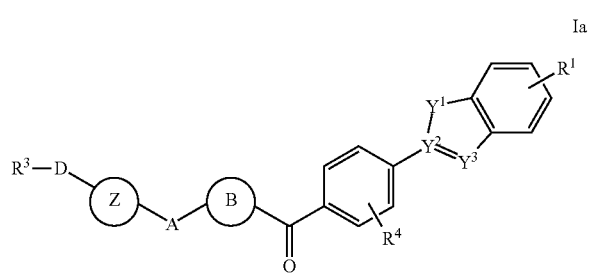

or a salt thereof, wherein R$^1$ is H, —Cl, —F, —Br, —I, —OH, —CN, —NO$_2$, substituted or unsubstituted C$_1$-C$_6$ alkyl, substituted or unsubstituted C$_1$-C$_6$ alkenyl, substituted or unsubstituted cycloalkyl, aryl or heteroaryl; R$^3$ is —[(CH$_2$)$_2$E]$_n$(CH$_2$)$_2$NR'R" and n is any integer from 0 through 30, wherein R' and R" are each independently H, substituted or unsubstituted C$_1$-C$_6$ alkyl, substituted or unsubstituted C$_1$-C$_6$ alkenyl, or substituted or unsubstituted cycloalkyl; R$^4$ is H, —Cl, —F, —Br, —I, —OH, —CN, —NO$_2$, substituted or unsubstituted C$_1$-C$_6$ alkyl, substituted or unsubstituted C$_1$-C$_6$ alkenyl, substituted or unsubstituted cycloalkyl, aryl or heteroaryl; Y$^1$ and Y$^3$ are independently C, O, N, NR$^2$ or S, wherein R$^2$ is H, —CH$_3$, —CH$_2$CH$_3$, —CH(CH$_3$)$_2$, —CH$_2$CH(CH$_3$)$_2$, —(CH)$_n$CH$_3$ wherein n is 1, 2, 3, 4 or 5, or —C(CH$_3$)$_3$; Y$^2$ is C or N; A and D are independently

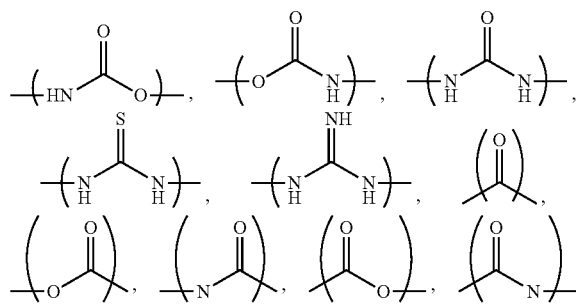

amidine, thioamide or A and/or D is absent; B is substituted or unsubstituted C$_4$-C$_9$-cycloalkyl, substituted or unsubstituted C$_4$-C$_9$-heterocycloalkyl comprising N, substituted or unsubstituted heteroaryl comprising N, S or O or B is absent; E is CH$_2$, O, NH or S, or E is absent; Z is substituted or unsubstituted aryl or substituted or unsubstituted heteroaryl comprising N, O or S, or Z is absent.

Related embodiments provide compounds of formula Ia as described above, wherein R$^1$ is H, —Cl, —F, —Br or —I, —OH, —CN, —NO$_2$, substituted or unsubstituted C$_1$-C$_6$ alkyl; R$^2$ is H, —CH$_3$, —CH$_2$CH$_3$, —CH(CH$_3$)$_2$, —CH$_2$CH(CH$_3$)$_2$, —(CH)$_n$CH$_3$ wherein n is 1, 2, 3, 4 or 5, or —C(CH$_3$)$_3$; R$^3$ is —[(CH$_2$)$_2$E]$_n$(CH$_2$)$_2$NR'R" and n is any integer from 0 through 12; R$^4$ is H, —Cl, —F, —Br, —I, —OH, —CN, —NO$_2$, substituted or unsubstituted C$_1$-C$_6$ alkyl; and Y$^1$ and Y$^3$ are independently C, O, N, NR$^2$ or S, wherein R$^2$ is H, substituted or unsubstituted C$_1$-C$_6$ alkyl, substituted or unsubstituted C$_1$-C$_6$ alkenyl, substituted or unsubstituted cycloalkyl, aryl or heteroaryl; and Y$^2$ is C or N; or a salt thereof.

Still other embodiments of the invention provide compounds according of formula Ib as shown below,

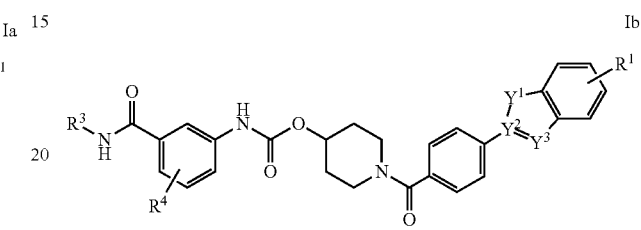

or a salt thereof, wherein R$^1$ is H, —Cl, —F, —Br, —I, —OH, —CN, —NO$_2$, substituted or unsubstituted C$_1$-C$_6$ alkyl, substituted or unsubstituted C$_1$-C$_6$ alkenyl, substituted or unsubstituted cycloalkyl, aryl or heteroaryl; R$^3$ is —[(CH$_2$)$_2$E]$_n$(CH$_2$)$_2$NR'R" and n is any integer from 0 through 30, wherein R' and R" are each independently H, substituted or unsubstituted C$_1$-C$_6$ alkyl, substituted or unsubstituted C$_1$-C$_6$ alkenyl, or substituted or unsubstituted cycloalkyl, and E is CH$_2$, O, NH or S, or E is absent; R$^4$ is H, —Cl, —F, —Br, —I, —OH, —CN, —NO$_2$, substituted or unsubstituted C$_1$-C$_6$ alkyl, substituted or unsubstituted C$_1$-C$_6$ alkenyl, substituted or unsubstituted cycloalkyl, aryl or heteroaryl; and Y$^1$ and Y$^3$ are independently C, O, N, NR$^2$ or S, wherein R$^2$ is H, substituted or unsubstituted C$_1$-C$_6$ alkyl, substituted or unsubstituted C$_1$-C$_6$ alkenyl, substituted or unsubstituted cycloalkyl, aryl or heteroaryl; and Y$^2$ is C or N.

Related embodiments provide compounds of formula Ib as described above, wherein R$^1$ is H, —Cl, —F, —Br or —I, —OH, —CN, —NO$_2$, substituted or unsubstituted C$_1$-C$_6$ alkyl; R$^2$ is H, —CH$_3$, —CH$_2$CH$_3$, —CH(CH$_3$)$_2$, —CH$_2$CH(CH$_3$)$_2$, —(CH)$_n$CH$_3$ wherein n is 1, 2, 3, 4 or 5, or —C(CH$_3$)$_3$; R$^3$ is —[(CH$_2$)$_2$E]$_n$(CH$_2$)$_2$NR'R" and n is any integer from 0 through 12; R$^4$ is H, —Cl, —F, —Br, —I, —OH, —CN, —NO$_2$, substituted or unsubstituted C$_1$-C$_6$ alkyl; Y$^1$ and Y$^3$ are independently C, O, N, NR$^2$ or S, wherein R$^2$ is H, substituted or unsubstituted C$_1$-C$_6$ alkyl, substituted or unsubstituted C$_1$-C$_6$ alkenyl, substituted or unsubstituted cycloalkyl, aryl or heteroaryl; and Y$^2$ is C or N; or a salt thereof.

Other embodiments provide compounds of formula Ic as shown below

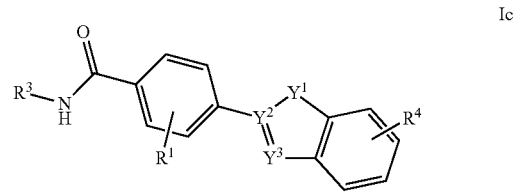

wherein $R^1$ is H, —Cl, —F, —Br, —I, —OH, —CN, —NO$_2$, substituted or unsubstituted C$_1$-C$_6$ alkyl, substituted or unsubstituted C$_1$-C$_6$ alkenyl, substituted or unsubstituted cycloalkyl, aryl or heteroaryl; $R^3$ is —[(CH$_2$)$_2$E]$_n$(CH$_2$)$_2$NR'R" and n is any integer from 0 through 30, wherein R' and R" are each independently H, substituted or unsubstituted C$_1$-C$_6$ alkyl, substituted or unsubstituted C$_1$-C$_6$ alkenyl, or substituted or unsubstituted cycloalkyl, and E is CH$_2$, O, NH or S, or E is absent; $R^4$ is H, —Cl, —F, —Br, —I, —OH, —CN, —NO$_2$, substituted or unsubstituted C$_1$-C$_6$ alkyl, substituted or unsubstituted C$_1$-C$_6$ alkenyl, substituted or unsubstituted cycloalkyl, aryl or heteroaryl; $Y^1$ and $Y^3$ are independently C, O, N, NR$^2$ or S, wherein $R^2$ is H, substituted or unsubstituted C$_1$-C$_6$ alkyl, substituted or unsubstituted C$_1$-C$_6$ alkenyl, substituted or unsubstituted cycloalkyl, aryl or heteroaryl; and $Y^2$ is C or N; or a salt thereof.

Related embodiments provide compounds of formula Ic as described above, wherein $R^1$ is H, —Cl, —F, —Br or —I; $R^2$ is H, —CH$_3$, —CH$_2$CH$_3$, —CH(CH$_3$)$_2$, —CH$_2$CH(CH$_3$)$_2$, —(CH)$_n$CH$_3$ wherein n is 1, 2, 3, 4 or 5, or —C(CH$_3$)$_3$; $R^3$ is —[(CH$_2$)$_2$E]$_n$(CH$_2$)$_2$NR'R" and n is any integer from 0 through 12; and $Y^1$ and $Y^3$ are independently C, O, NR$^2$ or S, wherein $R^2$ is H, substituted or unsubstituted C$_1$-C$_6$ alkyl, substituted or unsubstituted C$_1$-C$_6$ alkenyl, substituted or unsubstituted cycloalkyl, aryl or heteroaryl; and $Y^2$ is C or N; or a salt thereof.

Still other related embodiments provide compounds of formula I that are selected from,

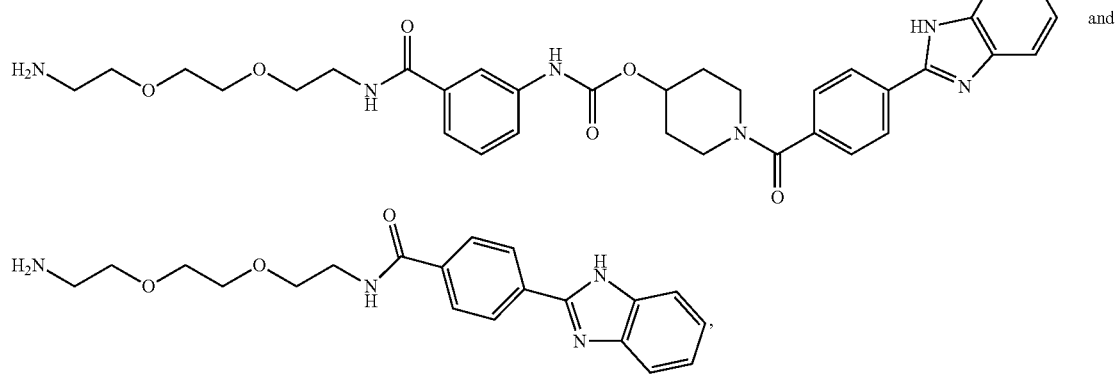

or a salt thereof.

Other embodiments of the invention provide compounds of formula II

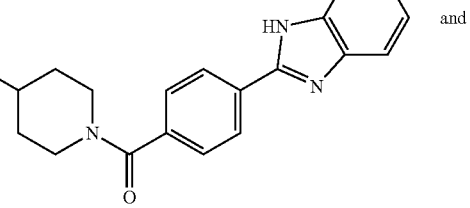
II or a salt thereof, wherein: $R^1$ is H, —Cl, —F, —Br, —I, —OH, —CN, —NO$_2$, substituted or unsubstituted C$_1$-C$_6$ alkyl, substituted or unsubstituted C$_1$-C$_6$ alkenyl, substituted or unsubstituted cycloalkyl, aryl or heteroaryl;

$R^3$ is —[(CH$_2$)$_2$E]$_n$(CH$_2$)$_2$NR'R" and n is any integer from 0 through 30, wherein R' and R" are each independently H, substituted or unsubstituted C$_1$-C$_6$ alkyl, substituted or unsubstituted C$_1$-C$_6$ alkenyl, or substituted or unsubstituted cycloalkyl;

aryl is any substituted or unsubstituted fully or partially aromatic hydrocarbon substituent or heteroaryl substituent;

$Y^1$ and $Y^3$ are independently C, O, N, NR$^2$ or S, wherein $R^2$ is H, substituted or unsubstituted C$_1$-C$_6$ alkyl, substituted or unsubstituted C$_1$-C$_6$ alkenyl, substituted or unsubstituted cycloalkyl, aryl or heteroaryl; and $Y^2$ is C or N;

A and D are independently

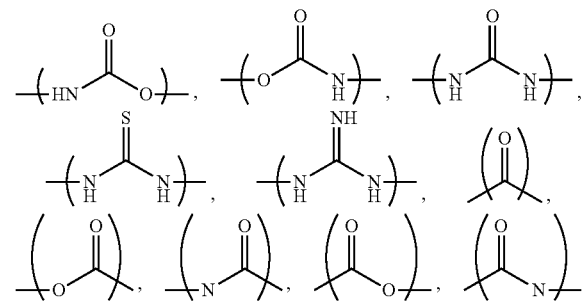

amidine, thioamide or A and/or D is absent;

B is substituted or unsubstituted C$_4$-C$_9$-cycloalkyl, substituted or unsubstituted C$_4$-C$_9$-heterocycloalkyl comprising N, O or S, substituted or unsubstituted heteroaryl comprising N, O, S or B is absent;

C is any of

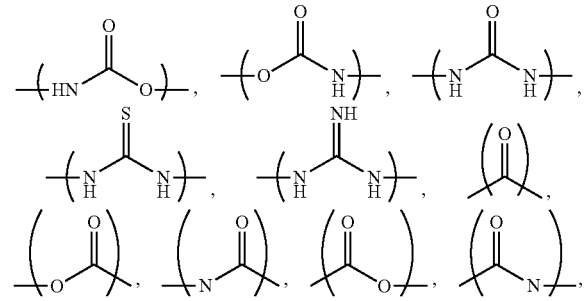

aryl, heteroaryl, amidine, thioamide or C is absent;

E is CH$_2$, O, NH or S, or E is absent;

Z is substituted or unsubstituted aryl, substituted or unsubstituted heteroalkyl comprising N, O or S, or substituted or unsubstituted heteroaryl comprising N, O, S or is Z is absent.

Related embodiments provide compounds of formula II, wherein $R^1$ is H, —Cl, —F, —Br or —I; $R^3$ is —[(CH$_2$)$_2$E]$_n$(CH$_2$)$_2$NR'R" and n is any integer from 0 through 12, wherein R' and R" are each independently H, —CH$_3$, —CH$_2$CH$_3$, —CH(CH$_3$)$_2$, —CH$_2$CH(CH$_3$)$_2$, —(CH)$_n$CH$_3$ wherein n is 1, 2, 3, 4 or 5, or —C(CH$_3$)$_3$; aryl is a substituted or unsubstituted phenyl, tolyl, xylyl, naphthyl, benzyl, thienyl, indolyl, pyrrolyl, pyridinyl, pyrimidinyl, purinyl, pyranyl, furanyl, thiophenyl, thiazolyl, imidazolyl, thioimidazolyl, oxazolyl, azepinyl, thiopenyl, thiazapinyl, quinolinyl, oxepinyl or oxadiazolyl group; $Y^1$ and $Y^3$ are independently C, O, N, NR$^2$ or S, wherein R$^2$ is H, —CH$_3$, —CH$_2$CH$_3$, —CH(CH$_3$)$_2$, —CH$_2$CH(CH$_3$)$_2$, —(CH)$_n$CH$_3$ wherein n is 1, 2, 3, 4 or 5, or —C(CH$_3$)$_3$; and $Y^2$ is C or N; A and D are independently

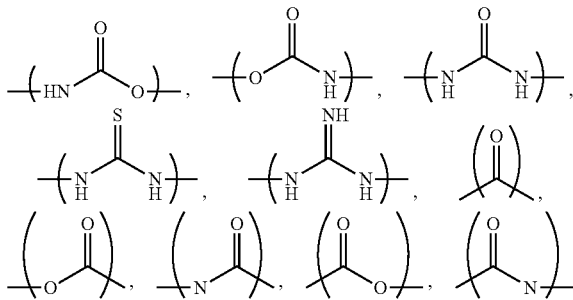

amidine, thioamide or A and/or D is absent; B is substituted or unsubstituted C$_4$-C$_9$-cycloalkyl, substituted or unsubstituted C$_4$-C$_9$-heterocycloalkyl comprising N, substituted or unsubstituted heteroaryl comprising N, S or O or B is absent; C is any of

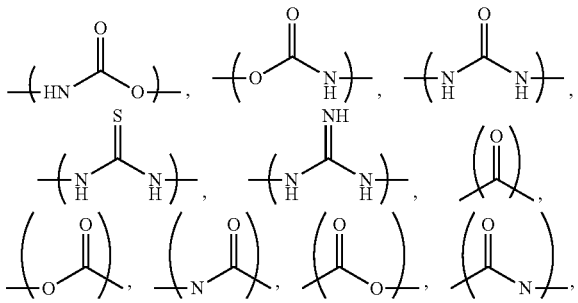

aryl, heteroaryl, amidine, thioamide or C is absent; E is CH$_2$, O, NH or S, or E is absent; Z is substituted or unsubstituted aryl or substituted or unsubstituted heteroaryl comprising N, O or S, or Z is absent; or a salt thereof.

Other embodiments provide compounds of formula IIa as shown below,

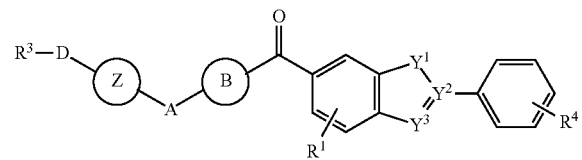

or a salt thereof, wherein $R^1$ is H, —Cl, —F, —Br, —I, —OH, —CN, —NO$_2$, substituted or unsubstituted C$_1$-C$_6$ alkyl, substituted or unsubstituted C$_1$-C$_6$ alkenyl, substituted or unsubstituted cycloalkyl, aryl or heteroaryl; $R^3$ is —[(CH$_2$)$_2$E]$_n$(CH$_2$)$_2$NR'R" and n is any integer from 0 through 30, wherein R' and R" are each independently H, substituted or unsubstituted C$_1$-C$_6$ alkyl, substituted or unsubstituted C$_1$-C$_6$ alkenyl, or substituted or unsubstituted cycloalkyl; $R^4$ is H, —Cl, —F, —Br, —I, —OH, —CN, —NO$_2$, substituted or unsubstituted C$_1$-C$_6$ alkyl, substituted or unsubstituted C$_1$-C$_6$ alkenyl, substituted or unsubstituted cycloalkyl, aryl or heteroaryl; $Y^1$ and $Y^3$ are independently C, O, N, NR$^2$ or S, wherein R$^2$ is H, substituted or unsubstituted C$_1$-C$_6$ alkyl, substituted or unsubstituted C$_1$-C$_6$ alkenyl, substituted or unsubstituted cycloalkyl, aryl or heteroaryl; and $Y^2$ is C or N; A and D are independently

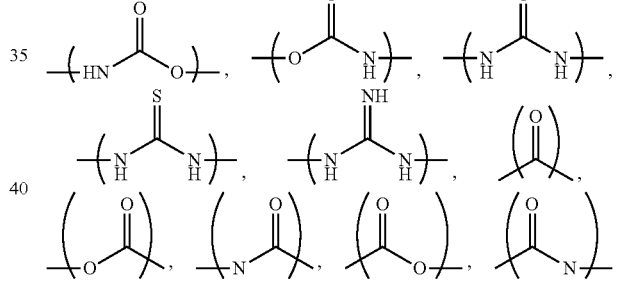

amidine, thioamide or A and/or D is absent; B is substituted or unsubstituted C$_4$-C$_9$-cycloalkyl, substituted or unsubstituted C$_4$-C$_9$-heterocycloalkyl comprising N, substituted or unsubstituted heteroaryl comprising N, S or O or B is absent; E is CH$_2$, O, NH or S, or E is absent; Z is substituted or unsubstituted aryl or substituted or unsubstituted heteroaryl comprising N, O or S, or Z is absent.

Still other embodiments provide compounds of formula IIb as shown below,

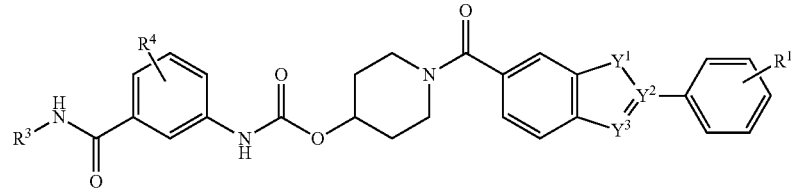

wherein $R^1$ is H, —Cl, —F, —Br, —I, —OH, —CN, —NO$_2$, substituted or unsubstituted C$_1$-C$_6$ alkyl, substituted or unsubstituted C$_1$-C$_6$ alkenyl, substituted or unsubstituted cycloalkyl, aryl or heteroaryl; $R^2$ is H, substituted or unsubstituted C$_1$-C$_6$ alkyl, substituted or unsubstituted C$_1$-C$_6$ alkenyl, substituted or unsubstituted cycloalkyl, aryl or heteroaryl; $R^3$ is —[(CH$_2$)$_2$E]$_n$(CH$_2$)$_2$NR'R" and n is any integer from 0 through 30, wherein R' and R" are each independently H, substituted or unsubstituted C$_1$-C$_6$ alkyl, substituted or unsubstituted C$_1$-C$_6$ alkenyl, or substituted or unsubstituted cycloalkyl; $R^4$ is H, —Cl, —F, —Br, —I, —OH, —CN, —NO$_2$, substituted or unsubstituted C$_1$-C$_6$ alkyl, substituted or unsubstituted C$_1$-C$_6$ alkenyl, substituted or unsubstituted cycloalkyl, aryl or heteroaryl; $Y^1$ and $Y^3$ are independently C, O, N, NR$^2$ or S, wherein $R^2$ is H, substituted or unsubstituted C$_1$-C$_6$ alkyl, substituted or unsubstituted C$_1$-C$_6$ alkenyl, substituted or unsubstituted cycloalkyl, aryl or heteroaryl; and $Y^2$ is C or N; E is CH$_2$, O, NH or S, or E is absent; or a salt thereof.

Related embodiments provide compounds or formula IIb as described above, wherein $R^1$ is H, —Cl, —F, —Br or —I; $R^2$ is H, —CH$_3$, —CH$_2$CH$_3$, —CH(CH$_3$)$_2$, —CH$_2$CH(CH$_3$)$_2$, —(CH)$_n$CH$_3$ wherein n is 1, 2, 3, 4 or 5, or —C(CH$_3$)$_3$; $R^3$ is —[(CH$_2$)$_2$E]$_n$(CH$_2$)$_2$NR'R" and n is any integer from 0 through 12; $Y^1$ and $Y^3$ are independently C, O, N, NR$^2$ or S, wherein $R^2$ is H, substituted or unsubstituted C$_1$-C$_6$ alkyl, substituted or unsubstituted C$_1$-C$_6$ alkenyl, substituted or unsubstituted cycloalkyl, aryl or heteroaryl; and $Y^2$ is C or N; or a salt thereof.

Other related embodiments provide compounds of formula IIc as shown below:

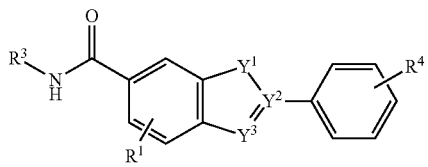

IIc or a salt thereof, wherein $R^1$ is H, —Cl, —F, —Br, —I, —OH, —CN, —NO$_2$, substituted or unsubstituted C$_1$-C$_6$ alkyl, substituted or unsubstituted C$_1$-C$_6$ alkenyl, substituted or unsubstituted cycloalkyl, aryl or heteroaryl; $R^2$ is H, substituted or unsubstituted C$_1$-C$_6$ alkyl, substituted or unsubstituted C$_1$-C$_6$ alkenyl, substituted or unsubstituted cycloalkyl, aryl or heteroaryl; $R^3$ is —[(CH$_2$)$_2$E]$_n$ (CH$_2$)$_2$NR'R" and n is any integer from 0 through 30, wherein R' and R" are each independently H, substituted or unsubstituted C$_1$-C$_6$ alkyl, substituted or unsubstituted C$_1$-C$_6$ alkenyl, or substituted or unsubstituted cycloalkyl; $R^4$ is H, —Cl, —F, —Br, —I, —OH, —CN, —NO$_2$, substituted or unsubstituted C$_1$-C$_6$ alkyl, substituted or unsubstituted C$_1$-C$_6$ alkenyl, substituted or unsubstituted cycloalkyl, aryl or heteroaryl; and $Y^1$ and $Y^3$ are independently C, O, N, NR$^2$ or S, wherein $R^2$ is H, substituted or unsubstituted C$_1$-C$_6$ alkyl, substituted or unsubstituted C$_1$-C$_6$ alkenyl, substituted or unsubstituted cycloalkyl, aryl or heteroaryl; and $Y^2$ is C or N; E is CH$_2$, O, NH or S, or E is absent.

Related embodiments provide compounds of formula IIc, wherein $R^1$ is H, —Cl, —F, —Br or —I, —OH, —CN, —NO$_2$, substituted or unsubstituted C$_1$-C$_6$ alkyl; $R^3$ is —[(CH$_2$)$_2$E]$_n$(CH$_2$)$_2$NR'R" and n is any integer from 0 through 12; $R^4$ is H, —Cl, —F, —Br or —I, —OH, —CN, —NO$_2$, substituted or unsubstituted C$_1$-C$_6$ alkyl; $Y^1$ and $Y^3$ are independently C, O, N, NR$^2$ or S, wherein $R^2$ is H, —CH$_3$, —CH$_2$CH$_3$, —CH(CH$_3$)$_2$, —CH$_2$CH(CH$_3$)$_2$, —(CH)$_n$CH$_3$ wherein n is 1, 2, 3, 4 or 5, or —C(CH$_3$)$_3$; and $Y^2$ is C or N S; or a salt thereof.

Still other related embodiments provide compounds of formula II as described above, wherein the compounds are selected from

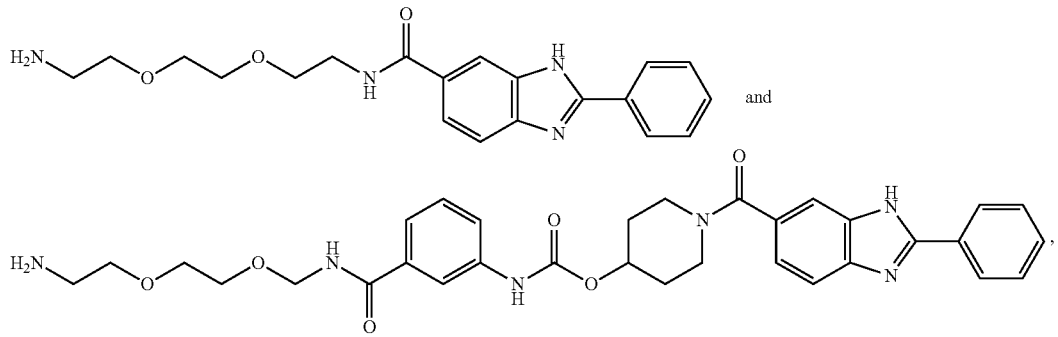

or a salt thereof.

In particular embodiments of the above-described compounds of formula I or II, each of D, Z, A, and B is absent.

Other embodiments provide a compound selected from the group consisting of:

N-(2-(2-(2-aminoethoxy)ethoxy)ethyl)-2-phenyl-1H-benzo[d]imidazole-6-carboxamide;

N-(2-(2-(2-aminoethoxy)ethoxy)ethyl)-4-(1H-benzo[d]imidazol-2-yl)benzamide;

1-(4-(1H-benzo[d]imidazol-2-yl)benzoyl)piperidin-4-yl (3-((2-(2-(2-aminoethoxy)ethoxy)ethyl)carbamoyl)phenyl)carbamate;

1-(2-phenyl-1H-benzo[d]imidazole-6-carbonyl)piperidin-4-yl (3-((2-(2-(2-aminoethoxy)ethoxy)ethyl)carbamoyl)phenyl)carbamate;

N-(2-(2-(2-aminoethoxy)ethoxy)ethyl)-2-(1'-(2-phenyl-1H-benzo[d]imidazole-6-carbonyl)-[4,4'-bipiperidin]-1-yl)benzo[d]thiazole-6-carboxamide;

N-(2-(2-(2-aminoethoxy)ethoxy)ethyl)-4-ethyl-2-(1'-(2-phenyl-1H-benzo[d]imidazole-6-carbonyl)-[4,4'-bipiperidin]-1-yl)thiazole-5-carboxamide;

2-(1'-(4-(1H-benzo[d]imidazol-2-yl)benzoyl)-[4,4'-bipiperidin]-1-yl)-N-(2-(2-(2-aminoethoxy)ethoxy)ethyl)benzo[d]thiazole-6-carboxamide; and 2-(1'-(4-(1H-benzo[d]imidazol-2-yl)benzoyl)-[4,4'-bipiperidin]-1-yl)-N-(2-(2-(2-aminoethoxy)ethoxy)ethyl)-4-ethylthiazole-5-carboxamide, or a salt thereof.

In another aspect, the invention provides compounds of formula III

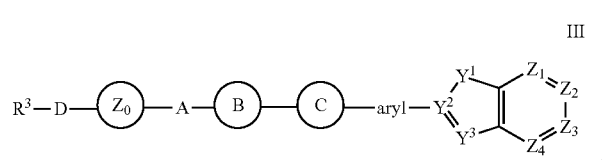

or formula IV

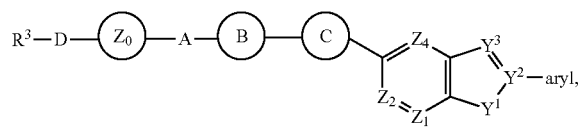

or a salt thereof, wherein:

each $Z_1$, $Z_2$, $Z_3$, and $Z_4$ is independently selected from N and $CR^1$ and no more than two of $Z_1$, $Z_2$, $Z_3$, and $Z_4$ are N, and each $R^1$ is independently selected from H, —Cl, —F, —Br, —I, —OH, —CN, —NO$_2$, substituted or unsubstituted $C_1$-$C_6$ alkyl, substituted or unsubstituted $C_1$-$C_6$ alkoxyl, substituted or unsubstituted $C_1$-$C_6$ alkenyl, substituted or unsubstituted cycloalkyl, aryl or heteroaryl;

$R^3$ is —[(CH$_2$)$_2$E]$_n$(CH$_2$)$_2$NR'R" and n is any integer from 0 through 30, wherein R' and R" are each independently H, substituted or unsubstituted $C_1$-$C_6$ alkyl, substituted or unsubstituted $C_1$-$C_6$ alkenyl, or substituted or unsubstituted cycloalkyl;

aryl is any substituted or unsubstituted fully or partially aromatic hydrocarbon substituent or heteroaryl substituent;

$Y^1$ and $Y^3$ are independently C, $CR^2$, O, N, $NR^2$ or S, wherein $R^2$ is H, substituted or unsubstituted $C_1$-$C_6$ alkyl, substituted or unsubstituted $C_1$-$C_6$ alkenyl, substituted or unsubstituted cycloalkyl, aryl or heteroaryl;

$Y^2$ is C;

A and D are independently

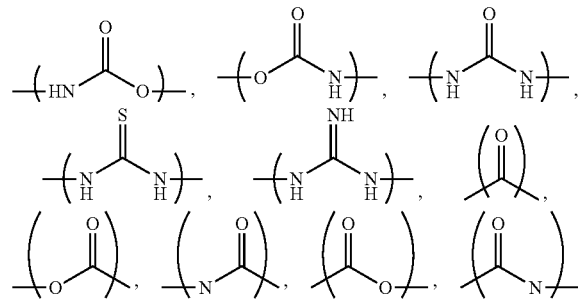

amidine, thioamide or A and/or D is absent;

B is substituted or unsubstituted $C_4$-$C_9$-cycloalkyl, substituted or unsubstituted $C_4$-$C_9$-heterocycloalkyl comprising N, O or S, substituted or unsubstituted heteroaryl comprising N, O, S or B is absent;

C is any of

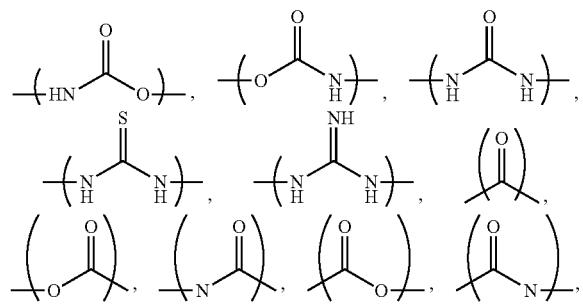

aryl, heteroaryl, amidine, thioamide;

E is CH$_2$, O, NH or S, or E is absent; and

Z is substituted or unsubstituted aryl, substituted or unsubstituted heteroalkyl comprising N, O or S, or substituted or unsubstituted heteroaryl comprising N, O, S or Z is absent. In still further embodiments, the invention provides compounds according to formula III and formula IV, above, wherein any of $Y^1$, $Y^2$, $Y^3$, aryl, C, B, A, $Z_0$ (Z), D, $R^3$ and/or E is as defined in any of the preceding embodiments describing compounds of formula I and/or II. In one such embodiment of the compound of formula III or IV, each of D, Z (or $Z_0$), A, and B is absent.

Synthetic Methods

Compounds described herein are prepared by using 1-[Bis(dimethylamino)methylene]-1H-1,2,3-triazolo[4,5-b]pyridinium 3-oxid hexafluorophosphate (HATU) to generate an active ester from a carboxylic acid on desired starting compounds, followed by treatment with N,N-diisopropylethylamine (DIPEA, also known as Hunig's base) to form amide bonds. Useful solvents for the reactions include dimethylformamide (DMF) and other polar organic solvents.

Affinity Chromatography

Affinity chromatography is used to separate a protein of interest from a solution comprising the protein and one or more impurities based on the affinity of the protein for a ligand that is covalently bound to a solid phase (chromatography column, resin, matrix, bead, gel, etc: used interchangeably). Proteins in the solution with weak affinity, or lacking affinity, for the ligand flow through the solid phase unimpeded, leaving the protein bound to the solid phase. The protein can then be eluted from the solid phase by decreasing the affinity of the protein for the ligand. The ligand comprises the compounds described herein.

The affinity chromatography ligand may be immobilized on a solid phase. By "solid phase" is meant a non-aqueous matrix to which the ligand can adhere (for example, a column, resin, matrix, bead, gel, etc), as described further herein. Exemplary materials and methods for ligand affinity chromatography and known in the art, e.g., as described in WO2011/012715, the contents of which are incorporated herein in their entirety. The solid phase is generally one which comprises for example, a glass, silica, agarose or polystyrene surface. The solid phase may be a purification column or a discontinuous phase of discrete particles. The solid phase may be a controlled pore glass column or a silicic acid column. The solid phase may be coated with a reagent (such as glycerol) which is intended to prevent nonspecific adherence of impurities to the solid phase. For example, the affinity solid phase may be agarose.

Typically, the material to be used as an affinity matrix is insoluble in the system in which the target molecule is found. Usually, but not always, the insoluble matrix is a solid. Hundreds of substances have been described and utilized as affinity matrices, including agarose, cellulose, dextran, polyacrylamide, latex, controlled pore glass. Useful affinity supports are those with a high surface-area to volume ratio, chemical groups that are easily modified for covalent attachment of ligands, minimal nonspecific binding properties, good flow characteristics and mechanical and chemical stability. Porous supports (also called resins or gels) generally provide the most useful properties for affinity purification of proteins. These types of supports are usually sugar- or acrylamide-based polymer resins that are produced in solution (i.e., hydrated) as 50-150 μm diameter beads. The beaded format allows these resins to be supplied as wet slurries that can be easily dispensed to fill and "pack" columns with resin beds of any size. The beads are porous and large enough that biomolecules (proteins, etc.) can flow as freely into and through the beads as they can between and around the surface of the beads. The affinity ligand is covalently attached to the bead polymer (external and internal surfaces) by various means. The result is a loose matrix in which sample molecules can freely flow past a high surface area of immobilized ligand. One of the most widely used matrix for protein affinity purification techniques is crosslinked beaded agarose (e.g., available in 4% and 6% densities). A 1 mL resin-bed is more than 90% water by volume. Beaded agarose is good for routine applications but crushes easily, making it suitable for gravity-flow, low-speed-centrifugation, and low-pressure procedures. Additional crosslinking and/or chemical hardening of beaded agarose resins can increase its ability to withstand higher pressures but can also result in lower the binding capacity. Resins based on polyacrylamide are also used as supports for column affinity chromatography. Such polyacrylamide resins may be used in medium pressure applications with a peristaltic pump or other liquid chromatography systems. Both agarose and polyacrylamide supports have low non-specific binding characteristics Magnetic particles are a completely different type of affinity support from beaded agarose and other porous resins. They are much smaller (typically 1-4 μm diameter) and solid (non-porous). Their small size provides the sufficient surface area-to-volume ratio needed for effective ligand immobilization and affinity purification. Magnetic beads are produced as superparamagnetic iron oxide particles that are covalently coated with silane derivatives. The coating makes the beads inert (i.e., to minimize nonspecific binding) and provides the particular chemical groups needed for attaching the affinity ligand. Affinity purification with magnetic particles is preferably not performed in-column. Instead, a few microliters of beads is mixed with several hundred microliters of sample as a loose slurry. During mixing, the beads remain suspended in the sample solution, allowing affinity interactions to occur with the immobilized ligand. After sufficient time for binding has been given, the beads are collected and separated from the sample using a powerful magnet. Typically, simple bench-top procedures are done in microcentrifuge tubes, and pipetting or decanting is used to remove the sample (or wash solutions, etc.) while the magnetic beads are held in place at the bottom or side of the tube with a suitable magnet. Advantages of magnetic particles over porous resins include the fact that magnetic beads exhibit less non-specific binding than porous supports, the fact that magnetic beads can be used for cell separation procedures, and the fact that magnetic beads are suitable for high-throughput automation. Sophisticated and powerful sample-handling instruments are available for performing assays and purification procedures using magnetic separations.

The affinity ligand may also be coupled to polymers, magnetic particles, latex beads, nanoparticles, macro-beads, membranes, microplates, array surfaces, dipsticks and a host of other devices that facilitate the capture of specific biomolecules.

The chemical reactions that make possible ligand attachment are known in the art, and well characterized. These reactions facilitate the attachment of biomolecules through their common chemical groups. The types of functionalities generally used for attachment include easily reactive components such as primary amines, sulfhydryls, aldehydes, and carboxylic acids. Usually, the solid phase matrix first is activated with a compound that is reactive toward one or more of these functional groups. The activated complex then can generate a covalent linkage between the ligand and the support, resulting in ligand immobilization.

For example, several effective beaded agarose, beaded acrylamide and magnetic bead affinity supports are commercially available in activated forms that are ready to use for coupling many different types of ligands. These activation chemistries and protocols have been optimized to assure excellent coupling yields and to generate stable covalent linkages that will not easily leach the immobilized ligand.

One common functional target for immobilizing molecules is the amine group ($-NH_2$). For example, NHS esters are reactive groups formed by EDC activation of carboxylate molecules. NHS ester-activated resins react with primary amines in slightly alkaline conditions (pH 7.2-8.5) to yield stable amide bonds. The immobilization reaction is usually performed in phosphate buffer at pH 7.2-8.0 for 0.5 to 4 hours at room temperature or 4° C. Primary amine buffers such as Tris (TBS) are not compatible because they compete for reaction; however, in some procedures, it is useful to add Tris or glycine buffer at the end of a conjugation procedure to quench (stop) the reaction. Another method of coupling amine containing compounds to beaded agarose resin involves a chemistry called reductive amination. Amines on the ligand compound conjugate with aldehyde groups of the support, which are prepared by mild oxidization of the agarose polysaccharide matrix. The immobilization reaction using reductive amination involves the formation of an initial Schiff base between the aldehyde and amine groups, which then is reduced to a secondary amine by the addition of sodium cyanoborohydride ($NaCNBH_3$). Depending on the type and amount of ligand present, a coupling reaction using reductive amination can achieve immobilization yields of greater than 85%. Another amine-reactive strategy that can be used for immobilization is the azlactone ring. This is a unique, durable polyacrylamide-like resin formed by co-polymerization of acrylamide with azlactone. A primary amine will react with an azlactone group in a ring-opening process that produces an amide bond at the end of a five-atom spacer. The group is spontaneously reactive with amines; no additives or catalysts are needed to drive the coupling process. Adding a quantity of the support to a sample containing an amine-containing molecule causes immobilization to occur within about an hour. Another method for immobilizing amine-containing affinity ligands is the use of carbonyl diimidazole (CDI) to activate hydroxyls on agarose supports to form reactive imidazole carbamates. This reactive group is formed on the support in organic solvent and stored as a suspension in acetone to prevent hydrolysis. Reaction of the support in an aqueous coupling buffer with primary amine-containing ligands causes loss of the imidazole groups and formation of carbamate linkages. The coupling process occurs at basic pH (8.5-10), but it is a slower reaction with proteins than reductive amination or azlactone coupling. CDI-activated resins are particularly useful for immobilizing peptides and small organic molecules. The reaction also can be done in organic solvent to permit coupling of water-insoluble ligands.

The affinity ligand may also be immobilized through functional groups other than just amines. In particular, the thiol group (—SH) can be used to direct coupling reactions away from active centers or binding sites on certain protein molecules. Thiol groups (sulfhydryls) can be indigenous within an affinity ligand molecule, or they may be added by synthetic chemistry methods known in the art.

Methods for coupling thiol group containing ligands are known in the art. For example, maleimide-activated reagents react specifically with sulfhydryl groups (—SH) at near neutral conditions (pH 6.5-7.5) to form stable thioether linkages. The maleimide chemistry is the basis for most crosslinkers and labeling reagents designed for conjugation of sulfhydryl groups. The method is particularly useful for coupling thiol containing ligands to maleimide-activated polystyrene microplates; e.g. to effectively coat the plate surface with ligand. Iodoacetyl-activated supports (e.g., beaded agarose or acrylamide with an iodoacetyl group at the end of a long spacer arm) can be used to react with sulfhydryl groups of the affinity ligand at physiologic to alkaline conditions (pH 7.2 to 9), resulting in stable thioether linkages. Immobilization of sulfhydryls occurs through displacement of the iodine atom. In addition, pyridyl disulfide containing supports can be used to react with affinity ligand sulfhydryl groups over a broad pH range to form disulfide bonds. As such, conjugates prepared using this chemistry are cleavable with typical disulfide reducing agents, such as dithiothreitol (DTT). For this application, an amine-activated resin can be modified with a crosslinker to make an activated resin for reversible sulfhydryl immobilization.

The affinity ligand compound may also contain, or be modified to contain, carbonyl ketones or aldehydes in their native state. For example, glycoconjugates, as for glycoproteins or glycolipids, can be created that contain sugar residues that have hydroxyls on adjacent carbon atoms; these cis-diols can be oxidized with sodium periodate to create aldehydes as sites for covalent immobilization. Hydrazide-activated resins and compounds will conjugate with carbonyls of oxidized carbohydrates (sugars) at pH 5 to 7, resulting in formation of hydrazone bonds. Hydrazide chemistry is useful for labeling, immobilizing or conjugating glycoconjugates through glycosylation sites.

The affinity ligand compound may also contain, or be modified to allow for coupling through a carboxyl group through the use of a carbodiimide-mediated reaction. Although no activated support contains a reactive group that is spontaneously reactive with carboxylates, chromatography supports containing amines (or hydrazides) can be used to form amide bonds with carboxylates that have been activated with the water-soluble carbodiimide crosslinker. EDC carbodiimide crosslinker for carboxyl-to-amine cross-linking EDC and other carbodiimides are zero-length cross-linkers; they cause direct conjugation of carboxylates (—COOH) to primary amines (—NH$_2$) without becoming part of the final crosslink (amide bond) between target molecules. Ligand immobilization may be achieved using diaminodipropylamine (DADPA) agarose resin as the primary amine for this reaction.

Coupling may also be achieved through reactive hydrogen chemistry. Small organic ligand affinity molecules may have structures that contain no available chemical handles for immobilization. Other molecules have functional groups that have low reactivity or are sterically hindered. However, some of these compounds have active (or replaceable) hydrogens that can be condensed with formaldehyde and an amine using the Mannich reaction. Formally, the Mannich reaction consists of the condensation of formaldehyde (or another aldehyde) with ammonia and another compound containing an active hydrogen. Instead of using ammonia, this reaction can be done with primary or secondary amines or even with amides. Ligand immobilization occurs when diaminodipropylamine (DADPA) agarose resin is used as the primary amine for this reaction. The affinity chromatography ligand solid phase allows for the separation of a protein sample based on a highly specific binding interaction between the protein of interest and the ligand solid phase. Thus, the solid phase comprises a ligand to which the protein of interest is capable of reversibly affixing, depending upon the buffer conditions.

The affinity ligand may also be immobilized through other known covalent linkages, such as ether (including thioether) and amide bonds.

Binding of the protein of interest to the ligand solid phase may be via column chromatography. For example, the ligand solid phase is formed into a column, a sample containing a protein of interest is flowed through the column, the column is washed with one or more wash solutions, followed by elution of the protein of interest from the column using an elution buffer.

The protein of interest may comprise plasma proteins, including serum albumin (particularly human HSA), immunoglobulin, fibrinogen, α1-acid glycoproteins, etc; enzymes including amylase, cellulase, calf-intestinal alkaline phosphatase (CIAP), lactate dehydrogenase (LDH), etc.; and artificial proteins or protein domains, particularly serum albumin fusion proteins, especially HSA fusion proteins (e.g., HSA-GLP1 fusions such as albiglutide), but also including affinity tagged proteins or domains (such as with 6His, FLAG, GST, etc.), Fc-fusion proteins, domain antibodies, etc. that comprise albumin. For example, the protein of interest may comprise human serum albumin. The compounds described herein may show specific binding to human serum albumin, and non-specific binding to rat or mouse serum albumin.

"Impurity" refers to any foreign or undesirable molecule that is present in the sample prior to affinity chromatography or following affinity chromatography in the sample eluate. There may be "process impurities" present. These are impurities that are present as a result of the process in which the protein of interest is produced. For example, these include host cell proteins (HCP), RNA, and DNA (for example viruses). "HCP" refers to proteins, not related to the protein of interest, produced by the host cell during cell culture or fermentation, including intracellular and/or secreted proteins. An example of a host cell protein is a protease, which can cause damage to the protein of interest if still present during and after purification. For example, if a protease remains in the sample comprising the protein of interest, it can create product-related substances or impurities which were not originally present. The presence of proteases can cause decay of the protein of interest over time during the purification process, and/or in the final formulation. Removal of HCP, or reduced levels of HCP, by definition equals removal or reduction of proteases.

Process impurities also include components used to grow the cells or to ensure expression of the protein of interest, for example, solvents (e.g. methanol used to culture yeast cells), antibiotics, methotrexate (MTX), media components, flocculants, etc. Also included are molecules that are part of the affinity chromatography ligand solid phase that may leach into the sample during prior steps.

Impurities also include "product-related substances" which include proteins that retain their activity but are different in their structure; and "product-related impurities" which include proteins that have lost their activity because of their difference in structure. These product-related variants include, for example, high molecular weight species (HMWs), low molecular weight species (LMWs), aggregated proteins, precursors, degraded proteins, misfolded proteins, underdisulfide-bonded proteins, fragments, and deamidated species.

Compounds of Formula I II, III and IV as Half-Life Extenders for Therapeutic Agents Compounds of formula I, II, III or IV as described herein may be conjugated, via covalent or non-covalent interactions, to therapeutic agents, including peptide and polypeptide therapeutic agents.

As used herein, "therapeutic agent" refers to any drug (for example, a small organic molecule, a nucleic acid, a polypeptide) that can be administered to an individual to produce a beneficial therapeutic or diagnostic effect through binding to and/or altering the function of a biological target molecule in the individual. Potential therapeutic agents include exendins, insulin, protease inhibitors, hormones, vasopressin, immunoglobulins, buserelin, 9-desglycinamide, 8-arginine vasopressin (DGAVP), AL-108, phylomers, osteocalcin, peptidomimetic compounds such as ApoA1 mimetics including D-4F, antibody- and antibody fragment-based therapeutics, and any other peptide, polypeptide or small molecule compound that can be conjugated to the compounds herein. Suitable conjugation materials and methods are known in the art, and further described in WO2003/084469, WO2012/140647, and WO2014/106583, the contents of which are incorporated herein in their entirety. Suitable therapeutic agents may be administered with compounds of formula I, II, III or IV, by any suitable administration route including orally, intravenously, nasally, interperatoneally, subcutaneously, and orally. The therapeutic agent and compound of formula I, II, III or IV then associates with a plasma protein in the blood, such that the resulting complex acts to extend the plasma half-life of the therapeutic agent. The plasma protein in the blood may be albumin. For example, the plasma protein may be human serum albumin. The compounds described herein may show specific binding to human serum albumin, and non-specific binding to rat or mouse serum albumin.

The phrases, "half-life" ("t½") and "serum half life", refer to the time taken for the serum (or plasma) concentration of the conjugated therapeutic agent in accordance with the disclosure to reduce by 50%, in vivo, for example due to degradation of the therapeutic agent and/or clearance or sequestration of the antigen binding protein by natural mechanisms.

Measuring Half-Life

Half-life (t½): refers to the time required for the concentration of the conjugated therapeutic agent to reach half of its original value. The serum half-life of proteins can be measured by pharmacokinetic studies.

Clearance (CL): refers to the volume of plasma irreversibly cleared of a protein per unit time. Clearance is calculated as the Dose/AUC (AUC: is the Area Under Curve or Area under the plasma drug concentration time curve). Clearance can also be calculated by the rate of drug elimination divided by the plasma concentration of the conjugated therapeutic agent (rate of elimination=CL*concentration).

Mean Residence Time (MRT): The average time that the conjugated therapeutic agent resides in the body before being irreversibly eliminated. Calculated as MRT=AUMC/AUC.

Steady state concentration: The steady state concentration (Css) is the concentration reached when the drug elimination rate becomes equal to drug administration rate as a result of continued drug administration. Css fluctuates between peak and trough levels and is measured in microgram/ml. "Mean steady-state trough concentration" refers to the mean of the trough level across the patient population at a given time.

EXAMPLES

Example 1

Preparation of N-(2-(2-(2-aminoethoxy)ethoxy)ethyl)-4-(1H-benzo[d]imidazol-2-yl)benzamide (compound 4) and N-(2-(2-(2-aminoethoxy)ethoxy)ethyl)-2-phenyl-1H-benzo[d]imidazole-6-carboxamide (compounds 5)

To a solution of the desired carboxylic acid (1.0 equiv, 0.201 mmol) and HATU (92 mg, 0.242 mmol) in N,N-dimethylformamide (DMF) (3 mL) at rt was added DIPEA (0.106 mL, 0.604 mmol) and stirred for 10 minutes. To the solution was then added tert-butyl (2-(2-(2-aminoethoxy)ethoxy)ethyl)carbamate (0.048 mL, 0.201 mmol) and the reaction was allowed to stir at rt overnight. The reaction was diluted with ethyl acetate (EtOAc) (100 mL) and washed with NH$_4$Cl (2×100 mL) and saturated NaCl (1×50 mL). The organic layer was dried over MgSO$_4$ and then evaporated to dryness.

To a solution of the BOC protected material (1.0 equiv, 0.201 mmol) in dichloromethane (DCM) (3 mL) at rt was added TFA (0.465 ml, 6.03 mmol). The reaction was allowed to stir at rt for 1 hour. The solvent and excess TFA was removed under reduced pressure conditions and the obtained residue was azeotroped with DCM two times. The resulting material was dissolved in DMF then purified by preparatory HPLC.

Scheme 1 below shows the preparation of N-(2-(2-(2-aminoethoxy)ethoxy)ethyl)-4-(1H-benzo[d]imidazol-2-yl)benzamide (compound 4) and N-(2-(2-(2-aminoethoxy)ethoxy)ethyl)-2-phenyl-1H-benzo[d]imidazole-6-carboxamide (compound 5) from tert-butyl (2-(2-(2-aminoethoxy)ethoxy)ethyl)carbamate (1) and 4-(1H-benzo[d]imidazol-2-yl)benzoic acid (2) and 2-phenyl-1H-benzo[d]imidazole-6-carboxylic acid (3).

SCHEME 1

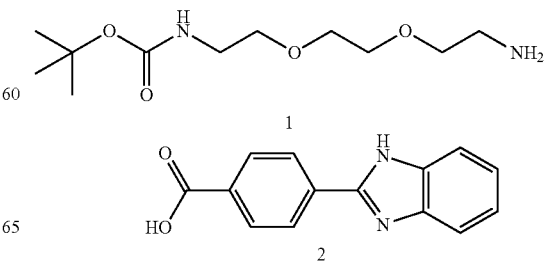

-continued

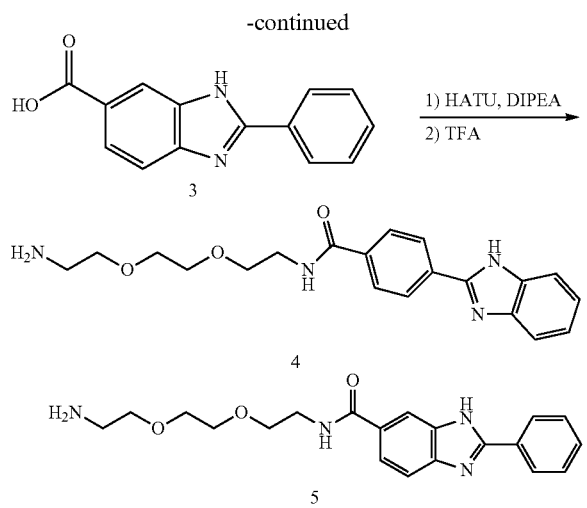

Example 2

Preparation of 1-(4-(1H-benzo[d]imidazol-2-yl)benzoyl)piperidin-4-yl (3-((2-(2-(2-aminoethoxy)ethoxy)ethyl)carbamoyl)phenyl)carbamate (compound 10) and 1-(2-phenyl-1 H-benzo[d]imidazole-6-carbonyl)piperidin-4-yl(3-((2-(2-(2-aminoethoxy)ethoxy)ethyl)carbamoyl)phenyl)carbamate (compound 11)

To a solution of the desired carboxylic acid (1.0 equiv, 0.420 mmol) and HATU (160 mg, 0.420 mmol) in N,N-Dimethylformamide (DMF) (3 mL) at rt was added DIPEA (0.220 mL, 1.259 mmol) and stirred for 10 minutes. To the solution was then added methyl 3-(((piperidin-4-yloxy)carbonyl)amino)benzoate (compound 7), 0.112 mL, 0.420 mmol) and the reaction was allowed to stir at rt overnight. The reaction was diluted with EtOAc (100 mL) and washed with NH₄Cl (2×100 mL) and saturated NaCl (1×50 mL). The organic layer was dried over MgSO₄ and then evaporated to dryness.

The resulting product was used as is, and dissolved in tetrahydrofuran (THF) (4 mL) and methanol (1 mL). To this solution was added LiOH (0.030 g, 1.260 mmol) in water (1 mL). The reaction was allowed to stir at rt overnight. LCMS analysis showed complete conversion. To each reaction was added 1N HCl (5 mL), then the solvents were evaporated to dryness. The material was carried to next step as is.

Next, to the resulting carboxylic acid (1.0 equiv, 0.420 mmol) and HATU (192 mg, 0.504 mmol) in N,N-dimethylformamide (DMF) (3 mL) at rt was added DIPEA (0.220 mL, 1.260 mmol) and stirred for 10 minutes. To this solution was then added tert-butyl (2-(2-(2-aminoethoxy)ethoxy)ethyl)carbamate (compound 1), (0.100 mL, 0.420 mmol) and the reaction was allowed to stir at rt overnight. The reaction was diluted with EtOAc (100 mL) and washed with NH₄Cl (2×100 mL) and saturated NaCl (1×50 mL). The organic layer was dried over MgSO₄ and then evaporated to dryness.

To the resulting BOC protected material (1.0 equiv, 0.360 mmol) in dichloromethane (DCM) (3 mL) at rt was added TFA (0.969 mL, 12.58 mmol). The reaction was allowed to stir at rt for 1 hour. The solvent and excess TFA was removed under reduced pressure conditions and the obtained residue was azeotroped with DCM two times. The resulting material was dissolved in DMF and then purified by preparatory HPLC.

Scheme 2 below shows the preparation of 1-(4-(1H-benzo[d]imidazol-2-yl)benzoyl)piperidin-4-yl (3-((2-(2-(2-aminoethoxy)ethoxy)ethyl)carbamoyl)phenyl)carbamate (compound 8) and 1-(2-phenyl-1 H-benzo[d]imidazole-6-carbonyl)piperidin-4-yl (3-((2-(2-(2-aminoethoxy)ethoxy)ethyl)carbamoyl)phenyl)carbamate (compound 9) from (2) 4-(1H-benzo[d]imidazol-2-yl)benzoic acid (3) 2-phenyl-1H-benzo[d]imidazole-6-carboxylic acid and (7) methyl 3-(((piperidin-4-yloxy)carbonyl)amino)benzoate. The reaction mixture of compounds (8) and (9) was then treated with LiOH as described to generate a mixture of 3-((((1-(4-(1H-benzo[d]imidazol-2-yl)benzoyl)piperidin-4-yl)oxy)carbonyl)amino)benzoic acid (10) and 3-((((1-(2-phenyl-1H-benzo[d]imidazole-6-carbonyl)piperidin-4-yl)oxy)carbonyl)amino)benzoic acid (11). Next, this mixture of products was treated with tert-butyl (2-(2-(2-aminoethoxy)ethoxy)ethyl)carbamate (1) 1-[Bis(dimethylamino)methylene]-1H-1,2,3-triazolo[4,5-b]pyridinium 3-oxid hexafluorophosphate (HATU) and N,N-diisopropylethylamine (DIPEA) as described, followed by treatment with trifluoroacetic acid (TFA) to generate the products 1-(4-(1H-benzo[d]imidazol-2-yl)benzoyl)piperidin-4-yl (3-((2-(2-(2-aminoethoxy)ethoxy)ethyl)carbamoyl)phenyl)carbamate (10) and 1-(2-phenyl-1H-benzo[d]imidazole-6-carbonyl)piperidin-4-yl (3-((2-(2-(2-aminoethoxy)ethoxy)ethyl)carbamoyl)phenyl)carbamate (11).

Scheme 2 below shows the preparation of carboxylates 8 and 9 over two steps from acids 2 and 3 respectively. Compounds 8 and 9 were then converted into the desired final products 1-(4-(1H-benzo[d]imidazol-2-yl)benzoyl)piperidin-4-yl (3-((2-(2-(2-aminoethoxy)ethoxy)ethyl)carbamoyl)phenyl)carbamate (10) and 1-(2-phenyl-1H-benzo[d]imidazole-6-carbonyl)piperidin-4-yl (3-((2-(2-(2-aminoethoxy)ethoxy)ethyl)carbamoyl)phenyl)carbamate (11) over two steps.

SCHEME 2

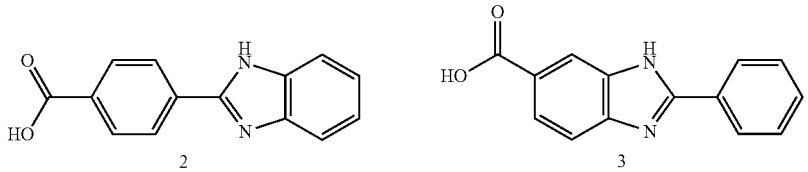

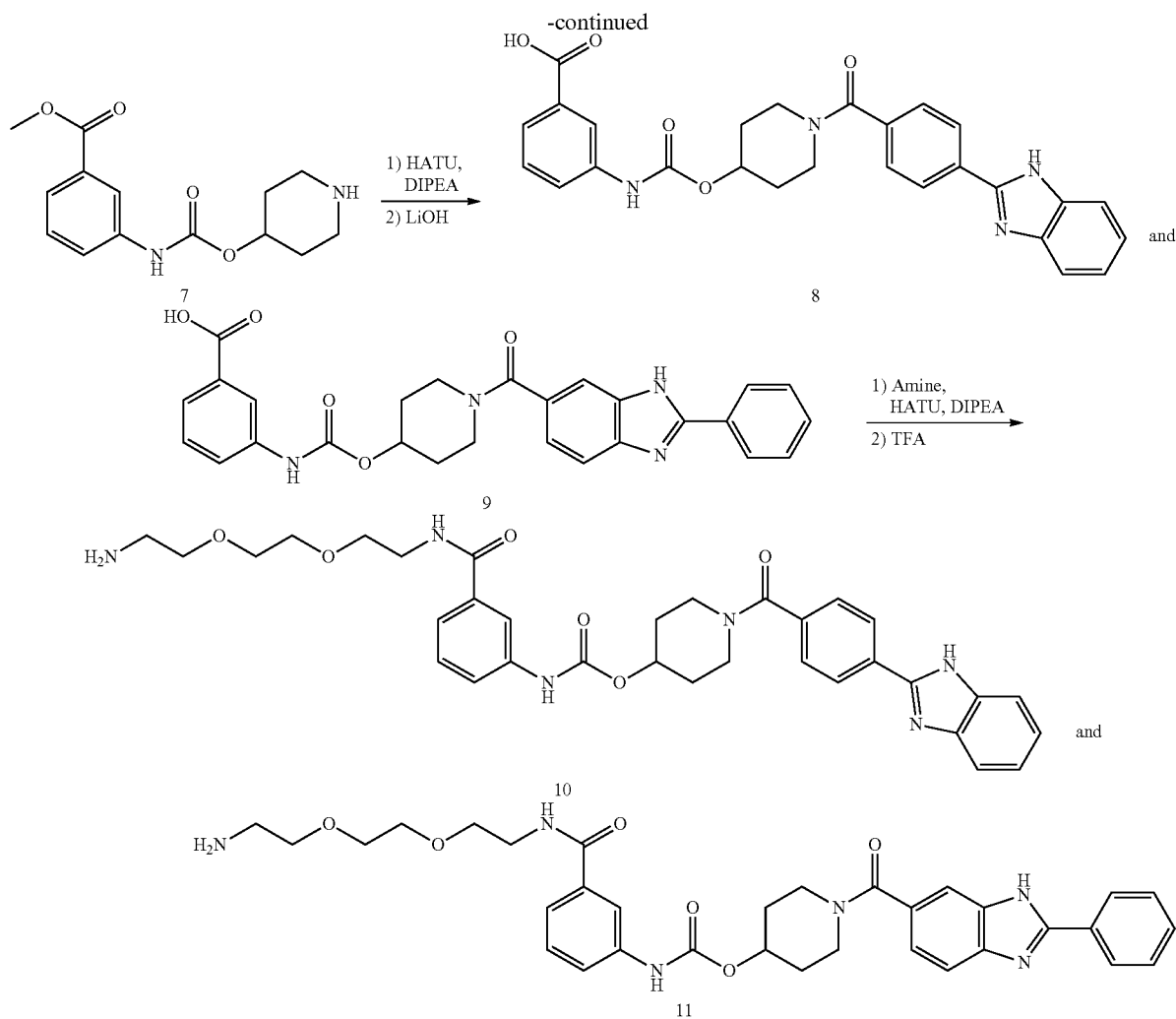

Example 3

Preparation of N-(2-(2-(2-aminoethoxy)ethoxy)ethyl)-2-(1'-(2-phenyl-1H-benzo[d]imidazole-6-carbonyl)-[4,4'-bipiperidin]-1-yl)benzo[d]thiazole-6-carboxamide (compound 19); N-(2-(2-(2-aminoethoxy)ethoxy)ethyl)-4-ethyl-2-(1'-(2-phenyl-1H-benzo[d]imidazole-6-carbonyl)-[4,4'-bipiperidin]-1-yl)thiazole-5-carboxamide (compound 20); 2-(1'-(4-(1H-benzo[d]imidazol-2-yl)benzoyl)-[4,4'-bipiperidin]-1-yl)-N-(2-(2-(2-aminoethoxy)ethoxy)ethyl)benzo[d]thiazole-6-carboxamide (compound 21); and 2-(1'-(4-(1H-benzo[d]imidazol-2-yl)benzoyl)-[4,4'-bipiperidin]-1-yl)-N-(2-(2-(2-aminoethoxy)ethoxy)ethyl)-4-ethylthiazole-5-carboxamide (compound 22)

To a solution of the desired carboxylic acid (e.g. compounds 2 and 3) (1.0 equiv, 0.420 mmol) and HATU (160 mg, 0.420 mmol) in N,N-Dimethylformamide (DMF) (3 mL) at rt was added DIPEA (0.220 mL, 1.259 mmol) and stirred for 10 minutes. To the solution was then added tert-butyl [4,4'-bipiperidine]-1-carboxylate (12) (0.108 mL, 0.420 mmol) and the reaction was allowed to stir at rt overnight. The reaction mixture was diluted with EtOAc (100 mL) and washed with NH$_4$Cl (2×100 mL) and saturated NaCl (1×50 mL). The organic layer was dried over MgSO$_4$ and then evaporated to dryness. The Boc protected crude material crude was dissolved in material dichloromethane (DCM) (3 mL). To the solution was added TFA (0.971 mL, 12.60 mmol). The reaction mixture was allowed to stir at rt 2 hours. The solvent and excess TFA was removed under reduced pressure condition and the obtained residue was azeotroped with DCM two time affording compounds 13 and 14 in quantitative yield.

Compounds such as 17 and 18 were prepared as described below. To a solution of the desired carboxylic acids (e.g. compounds 15 and 16) (1.0 equiv, 0.420 mmol) and HATU (0.192 g, 0.504 mmol) in N,N-Dimethylformamide (DMF) (3 mL) at rt was added DIPEA (0.220 mL, 1.260 mmol) and the mixture was stirred for 10 minutes. To the reaction mixture was then added tert-butyl (2-(2-(2-aminoethoxy)ethoxy)ethyl)carbamate (1) (0.100 mL, 0.420 mmol) and the reaction was allowed to stir at rt overnight. The reaction was diluted with EtOAc (100 mL) and washed with NH$_4$Cl (2×100 mL) and saturated NaCl (1×50 mL). The organic layer (containing compounds 17 and 18) was dried over MgSO$_4$ and then evaporated to dryness.

The resulting BOC-protected carboxylic acids (compounds 17 and 18) (1.0 equiv, 0.210 mmol) in N,N-Dimethylformamide (DMF) (3 mL) at rt was added DIPEA (1.5 mL, 0.315 mmol). To the solution was then added the desired amine (e.g. compounds 13 and 14) (1.0 equiv, 0.210 mmol) and the reaction was heated at 80 degrees overnight. The reaction was diluted with EtOAc (50 mL) and washed with NH$_4$Cl (2×50 mL) and saturated NaCl (1×50 mL). The organic layer (containing BOC-protected products 19, 20, 21, 22) was dried over MgSO$_4$ and then evaporated to dryness. The product was carried to next step without a need for purification. To a solution of the desired BOC-protected material (e.g. BOC-protected compounds 19, 20, 21 and 22) (1.0 equiv) in dichloromethane (DCM) (3 mL) at rt was added TFA (0.809 mL, 10.50 mmol). The reaction mixture was allowed to stir at rt for 1 hours. The solvent and excess TFA was removed under reduced pressure conditions and the obtained residue was azeotroped with DCM two times. The final products (e.g. compounds 19, 20, 21 and 22) were purified by prep HPLC.

Scheme 3 (below) describes preparation of compounds 19, 20, 21 and 22 in a three-part synthesis. First, compounds 13 and 14 are prepared from coupling of compounds 12 with acids 2 and 3 followed by BOC deprotection with TFA to afford compounds (4-(1H-benzo[d]imidazol-2-yl)phenyl)([4,4'-bipiperidin]-1-yl)methanone (13) and [4,4'-bipiperidin]-1-yl(2-phenyl-1H-benzo[d]imidazol-6-yl)methanone (14) in quantitative yields.

Compounds 17 and 18 were prepared through coupling of mono-protected diamine 1, with compound 15 (2-chlorobenzo[d]thiazole-6-carboxylic acid) and compound 16 (2-chloro-4-ethylthiazole-5-carboxylic acid) respectively.

Compounds 13 and 14 are then reacted with compounds 17 and 18 (in presence of base and heat to provide BOC protect final product which upon treatment with TFA afforded desired compounds N-(2-(2-(2-aminoethoxy)ethoxy)ethyl)-2-(1'-(2-phenyl-1H-benzo[d]imidazole-6-carbonyl)-[4,4'-bipiperidin]-1-yl)benzo[d]thiazole-6-carboxamide (19); N-(2-(2-(2-aminoethoxy)ethoxy)ethyl)-4-ethyl-2-(1'-(2-phenyl-1H-benzo[d]imidazole-6-carbonyl)-[4,4'-bipiperidin]-1-yl)thiazole-5-carboxamide (20); 2-(1'-(4-(1H-benzo[d]imidazol-2-yl)benzoyl)-[4,4'-bipiperidin]-1-yl)-N-(2-(2-(2-aminoethoxy)ethoxy)ethyl)benzo[d]thiazole-6-carboxamide (21); and 2-(1'-(4-(1H-benzo[d]imidazol-2-yl)benzoyl)-[4,4'-bipiperidin]-1-yl)-N-(2-(2-(2-aminoethoxy)ethoxy)ethyl)-4-ethylthiazole-5-carboxamide (22) in excellent yields.

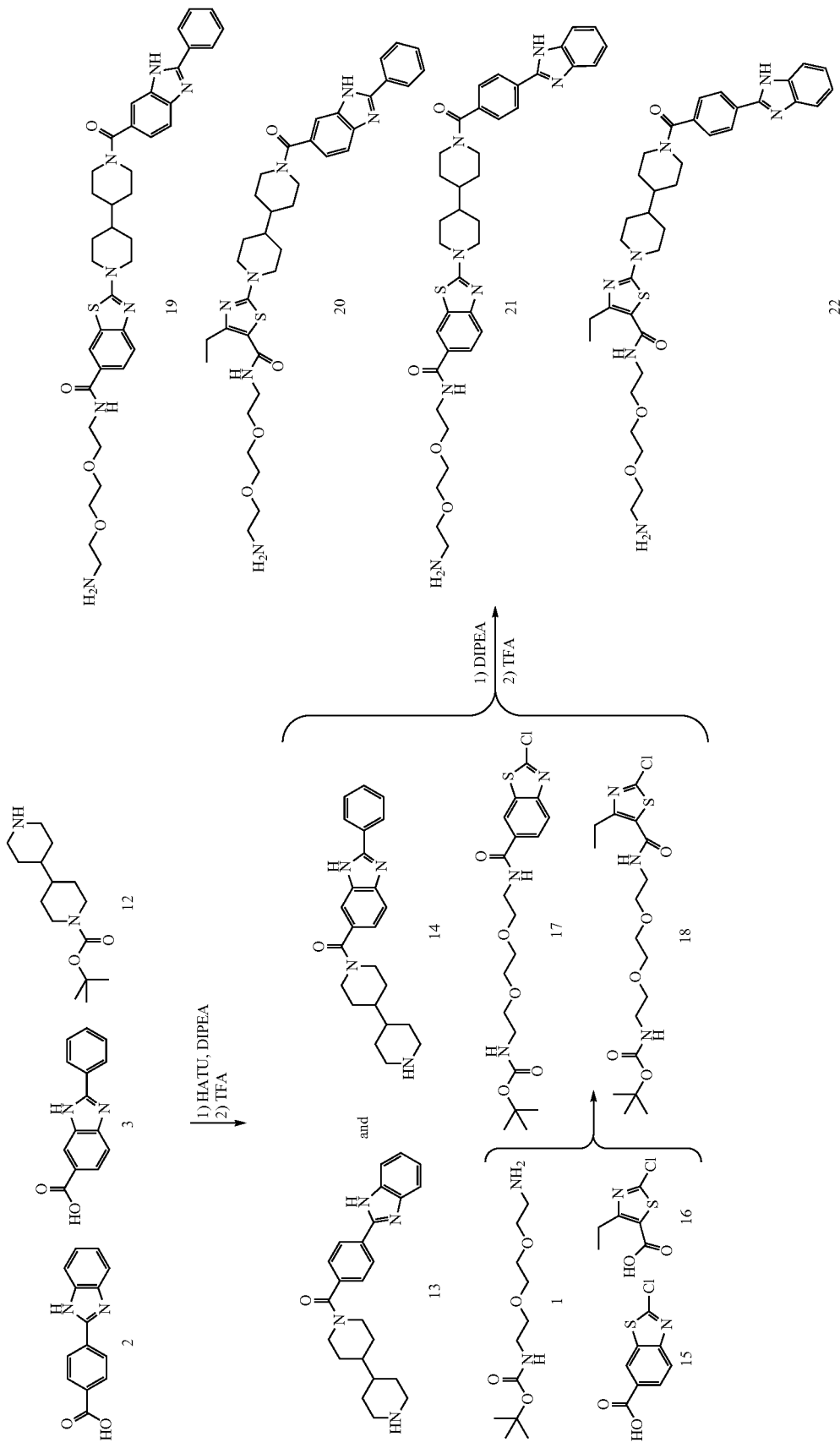
SCHEME 3

Affinity Examples

Example 4

Preparation of Affinity Agarose Material

Pierce NHS activated agarose (N-hydroxysuccinimide-activated agarose) (26 mg) was combined with 400 μL of a 100 μM solution of a compound of formula I or formula II as described herein, in phosphate-buffered saline (PBS) at pH 7.5 at RT for 1 h, followed by addition of 1M Tris-HCl at pH 8.0 for 30 min at RT. The resulting mixture yields approximately 200 μL of compound-conjugated agarose. FIG. 1 shows a schematic of the reaction and resulting conjugated agarose beads.

Example 5

Affinity Purification/Capture of Biomolecules

A. Cell Lysate Spiked with Human Serum Albumin

Figure 2:
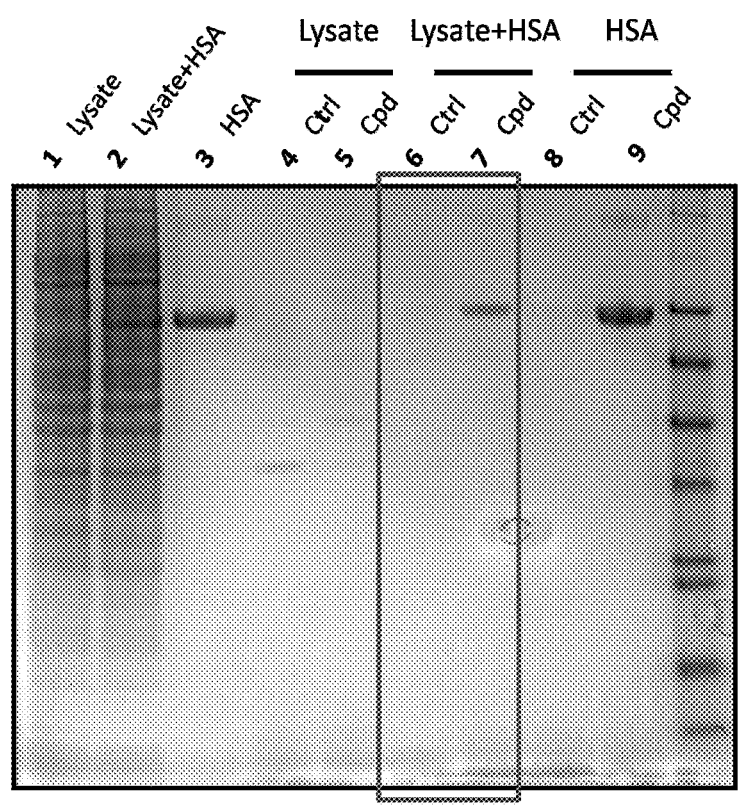
FIG. 2 shows a mini agarose gel where affinity agarose beads conjugated with a compound of formula I as described herein was used to separate/purify HSA from a cell lysate spiked with HSA.

Cell lysate was prepared by sonicating (MCF7 cells in PBS buffer $10^7$ cells were suspended in 500 μL PBS and sonicated on ice with a micro-sonication tip on a Branson Sonifier 450 (1 min at Output=4; Duty Cycle=30%) Once the solution turned clear, it was centrifuged at 13000 rpm for 20 minutes to remove debris, after which, 700 μg of the resulting lysate protein ($OD_{280}$) was spiked with 10 μg of HSA in 100 μL of PBS buffer, and this mixture was then loaded onto 5 μL of affinity agarose beads as prepared in Example 4. As shown in FIG. 2, the affinity agarose beads loaded with cell lysates+HSA effectively separated/captured the HSA from the cell lysates (compare lanes 6 and 7 (outlined) to lanes 8 and 9 immediately to the right, representing from left to right, respectively: HSA loaded onto agarose not conjugated to a compound as described herein, and HSA in the absence of cell lysate loaded onto conjugated affinity agarose beads).

B. Affinity Purification/Capture HSA Using Affinity Agarose Material Compared to Mimetic Blue®.

Figure 3:
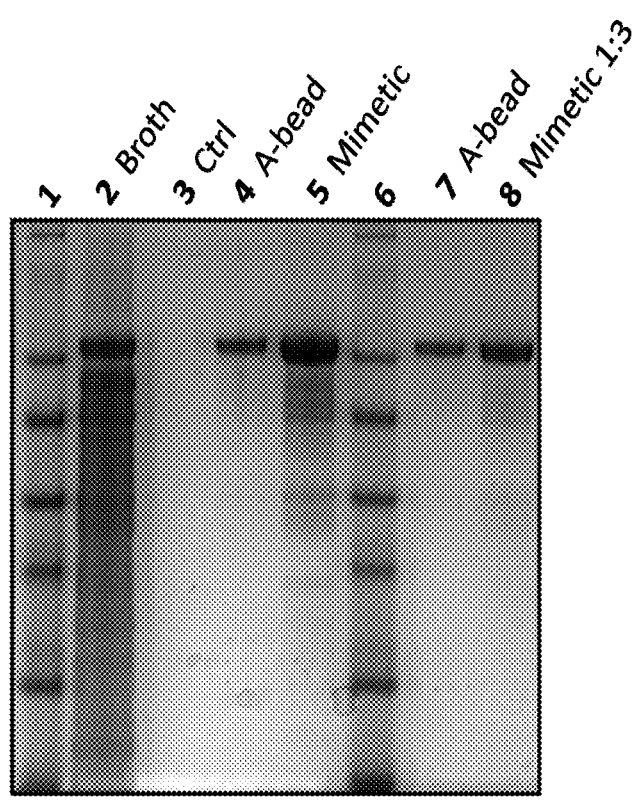
FIG. 3 shows the specificity of affinity agarose material conjugated to a compound of formula I for an HSA-fused peptide, compared to Mimetic Blue®.

FIG. 3 shows the superior specificity of affinity agarose material conjugated to a compound of formula I as described herein for HSA, compared to Mimetic Blue® for HSA (note lanes 4 and 7 labeled A-bead compared to lanes 5 and 8 labeled Mimetic).

C. Elution of Purified/Captured HSA-Fused Peptide

Another experiment compared the ability of various buffers and solutions to elute captured HSA from affinity agarose material conjugated to a compound of formula I as described in Example 4 In this experiment, six phynexus tips were packed with 5 uL of affinity agarose material as described herein. Each tip received 20 ug of HSA as input. The HSA was allowed to bind to the affinity agarose material at RT for 30 mins, after which representative flow-through was collected.

Each tip was washed twice with 50 uL washing buffer (PBS/$H_2O$ ratios of 100/0; 80/20; 60/40; 40/60; 20/80; and 0/100) for 10 min, each wash. Then the washing solution was collected and analyzed by SDS-PAGE. (Loaded (2% input and collected fractions to gel for lanes 2 and 3, respectively; loaded 13% to gel, lanes 4-15)

Figure 4A:
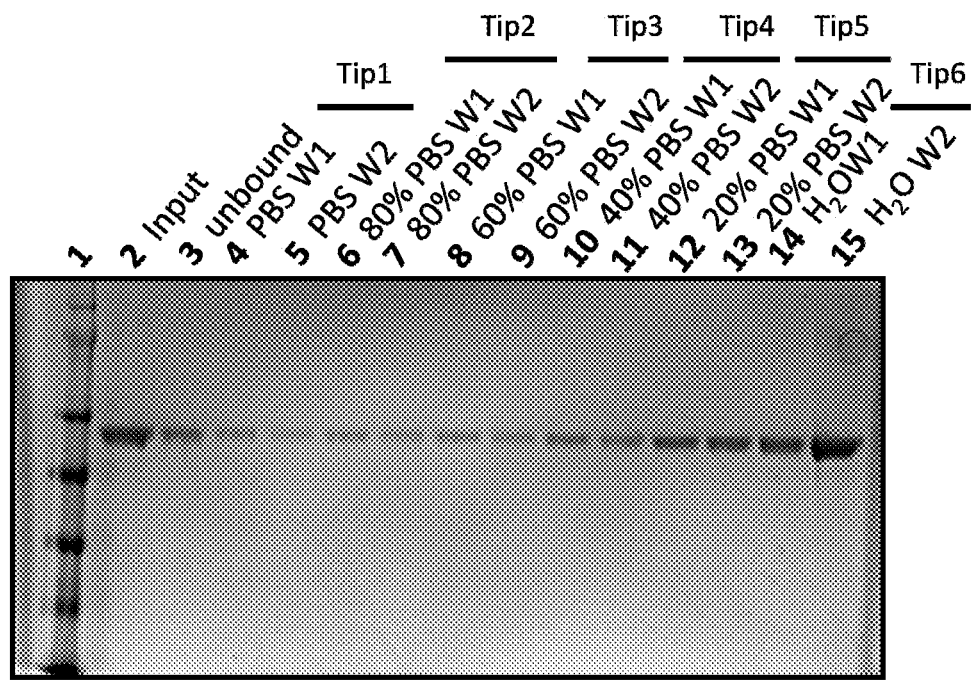
FIG. 4a shows a comparison of the effectiveness of different buffer solutions to elute HSA from affinity agarose material as described herein.
Figure 4B:
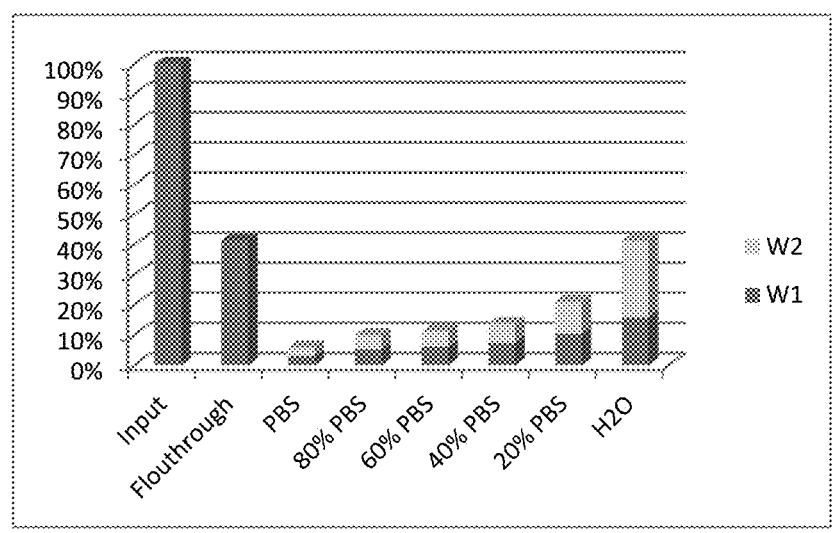

The amount of HSA in each gel band was quantified with FluoeChem software. As can be seen in lanes 14 and 15 of FIG. 4a, 60% elution was achieved with two washes using only $H_2O$ as the elution buffer (tip 6). In general, percent elution of HSA from the affinity agarose material described herein increased with decreasing ionic strength of the elution buffer (compare tip 1, lanes 4-5; tip 2, lanes 6-7; tip 3, lanes 8-9; tip 4, lanes 10-11; tip 5, lanes 12-13; and tip 6, lanes 14-15 of FIG. 4a; see also the results, as graphed in FIG. 4b, wherein wash 1 and 2 are combined and represented by dark and light shading, respectively, in each of lanes PBS through $H_2O$).

D. Effect of Heat on the Ability of Affinity Agarose Material to Capture an HSA-Fused Peptide Compared to Mimetic Blue®

Another experiment was performed comparing affinity agarose material conjugated to a compound of formula I as described in Example 4 with Mimetic Blue® that had been exposed to the HSA-fused peptide described above such that maximum binding capacity was achieved, after which the affinity agarose material plus biomolecule, or Mimetic Blue® plus biomolecule mixtures were heated at 95° C. in PBS (no detergent) for 10 min. After heat treatment, the HSA-fused peptide was eluted from the affinity agarose/biomolecule mixture or Mimetic Blue®/biomolecule mixture and the "eluted" fractions were analyzed and labeled as "bound".

Figure 5:
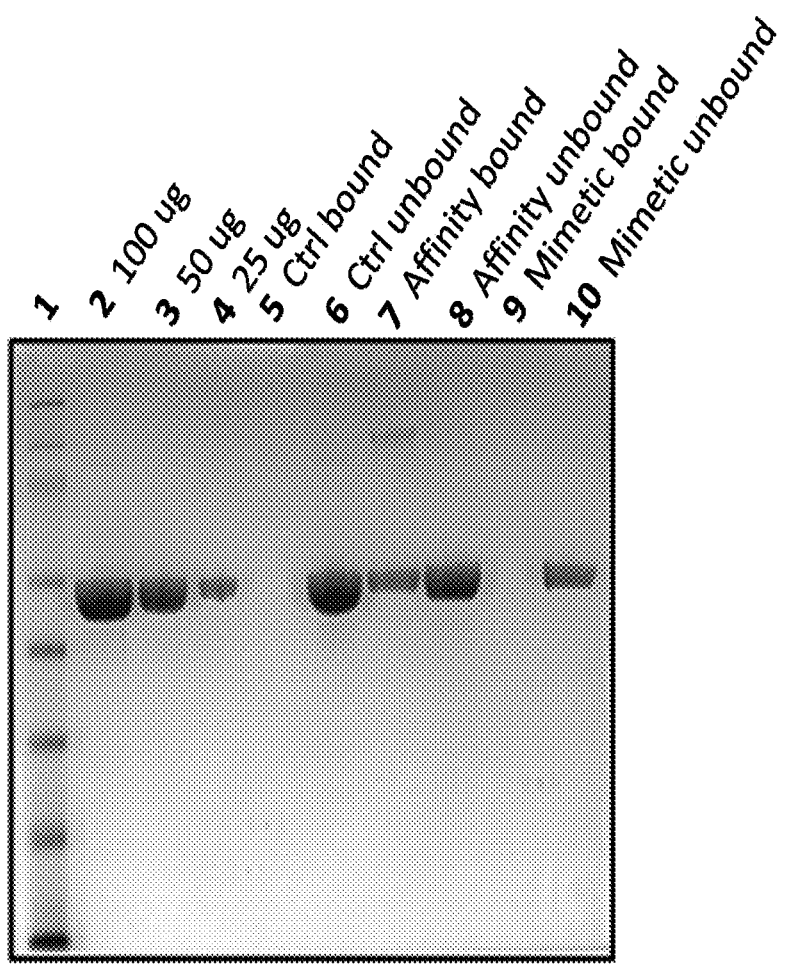
FIG. 5 shows a comparison of the effect of heat on binding of HSA to affinity agarose material conjugated to a compound of formula I versus binding of the same biomolecule to Mimetic Blue®.

As seen in FIG. 5, the affinity agarose material conjugated to a compound of formula I as described in Example 4 appears to have a different mechanism of action/binding than Mimetic Blue® (compare Affinity bound lane 7 to Mimetic Blue® bound lane 10) in that the association of the biomolecule to the affinity agarose material is breakable by heat, whereas the association of the biomolecule to Mimetic Blue® is not.

It should be noted that the biomolecule-spiked cell lysates or the biomolecule mixtures in buffer solutions as used in Examples 5A through 5D can be eluted with PBS (137 mM NaCl, 2.7 mM KCl, 10 mM $Na_2PO_4$, 10 mM $KH_2PO_4$ at pH 7.4) or RIPA buffer (50 mM Tris, 150 mM NaCl, 2 mM EDTA, 1% NP40, 0.5% NaDeoxycholate. 1% SDS at pH 8.0) or other low ionic strength buffer. Biomolecules may similarly be eluted from the affinity agarose material using such low ionic strength/low salt buffers, and may even be eluted with water, as exemplified in FIGS. 4a and 4b.

Half-Life Extension

Example 6

Compounds of Formula I, II, III, and IV as Half-Life Extenders for Therapeutic Molecules Compounds of formula I, II, III or IV as described herein may be conjugated, via covalent or non-covalent interactions, to therapeutic agents, particularly small molecule therapeutic agents having a functional moiety capable of conjugating with compounds of formula I, II, III or IV, including peptide and polypeptide therapeutic agents and oligonucleotide therapeutic agents.

In certain embodiments, the compounds of formulas I-IV associate with a plasma protein in the blood, such as human serum albumin (HSA) to form a binary affinity compound/serum protein conjugate, and this binary affinity compound/serum protein conjugate then interacts with the therapeutic agent, administered, for example orally or intravenously, once the therapeutic agent enters the circulation, to form a ternary complex, such that the resulting ternary complex acts to effectively prolong the plasma half-life of the therapeutic agent.

The embodiments of the invention described above are intended to be merely exemplary; numerous variations and modifications will be apparent to those skilled in the art. All such variations and modifications are intended to be within the scope of the present invention as defined in any appended claims.

What is claimed is:
1. A compound according to formula Ia as shown below,

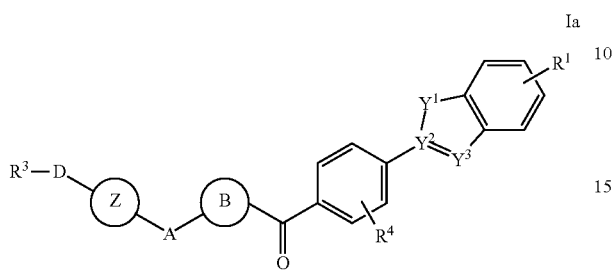

or a salt thereof, wherein:
$R^1$ is H, —Cl, —F, —Br, —I, —OH, —CN, —NO$_2$, substituted or unsubstituted $C_1$-$C_6$ alkyl, substituted or unsubstituted $C_2$-$C_6$ alkenyl, substituted or unsubstituted cycloalkyl, aryl or heteroaryl;
$R^3$ is —[(CH$_2$)$_2$E]$_n$(CH$_2$)$_2$NR'R" wherein n is any integer from 0 through 30, R' and R" are each independently H, substituted or unsubstituted $C_1$-$C_6$ alkyl, substituted or unsubstituted $C_2$-$C_6$ alkenyl, or substituted or unsubstituted cycloalkyl, and E is CH$_2$, O, NH or S, or E is absent;
$R^4$ is H, —Cl, —F, —Br, —I, —OH, —CN, —NO$_2$, substituted or unsubstituted $C_1$-$C_6$ alkyl, substituted or unsubstituted $C_2$-$C_6$ alkenyl, substituted or unsubstituted cycloalkyl, aryl or heteroaryl;
$Y^1$ and $Y^3$ are independently C, O, N, NR$^2$ or S, wherein $R^2$ is H, substituted or unsubstituted $C_1$-$C_6$ alkyl, substituted or unsubstituted $C_2$-$C_6$ alkenyl, substituted or unsubstituted cycloalkyl, aryl or heteroaryl;
$y^2$ is C or N;
A and D are independently

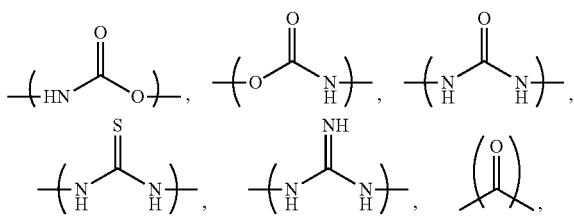

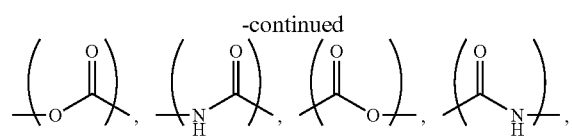

amidine, thioamide, or A and/or D is absent;
B is substituted or unsubstituted $C_4$-$C_9$-cycloalkyl, substituted or unsubstituted $C_4$-$C_9$-heterocycloalkyl comprising N, substituted or unsubstituted heteroaryl comprising N, S or O, or B is absent; and
Z is substituted or unsubstituted aryl or substituted or unsubstituted heteroaryl comprising N, O or S, or Z is absent.

2. A compound according to claim 1, or a salt thereof, wherein:
$R^1$ is H, —Cl, —F, —Br or —I;
$R^3$ is —[(CH$_2$)$_2$E]$_n$(CH$_2$)$_2$NR'R" wherein n is any integer from 0 through 12, R' and R" are each independently H, substituted or unsubstituted $C_1$-$C_6$ alkyl, substituted or unsubstituted $C_2$-$C_6$ alkenyl, or substituted or unsubstituted cycloalkyl, and E is CH$_2$, O, NG or S, or E is absent;
$Y^1$ and $Y^3$ are independently C, O, N, NR$^2$ or S, wherein $R^2$ is H, —CH$_3$, —CH$_2$CH$_3$, —CH(CH$_3$)$_2$, —CH$_2$CH(CH$_3$)$_2$, —(CH)$_m$CH$_3$ wherein m is 1, 2, 3, 4 or 5, or —C(CH$_3$)$_3$; and
$Y^2$ is C.

3. A compound of formula Ib as shown below,

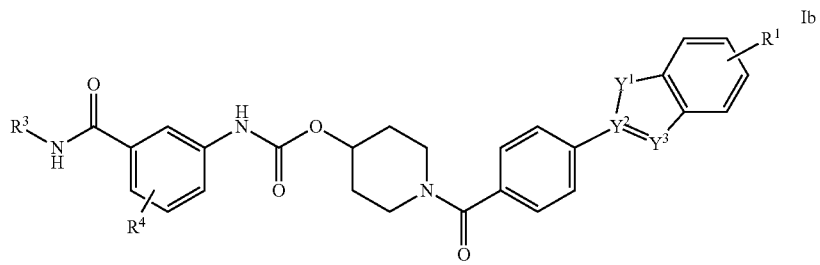

or a salt thereof, wherein:
$R^1$ is H, —Cl, —F, —Br, —I, —OH, —CN, —NO$_2$, substituted or unsubstituted $C_1$-$C_6$ alkyl, substituted or unsubstituted $C_2$-$C_6$ alkenyl, substituted or unsubstituted cycloalkyl, aryl or heteroaryl;
$R^3$ is —[(CH$_2$)$_2$E]$_n$(CH$_2$)$_2$NR'R" wherein n is any integer from 0 through 30, R' and R" are each independently H, substituted or unsubstituted $C_1$-$C_6$ alkyl, substituted or unsubstituted $C_2$-$C_6$ alkenyl, or substituted or unsubstituted cycloalkyl, and E is CH$_2$, O, NH or S, or E is absent;
$R^4$ is H, —Cl, —F, —Br, —I, —OH, —CN, —NO$_2$, substituted or unsubstituted $C_2$-$C_6$ alkenyl, substituted or unsubstituted $C_1$-$C_6$ alkenyl, substituted or unsubstituted cycloalkyl, aryl or heteroaryl;
$Y^1$ and $Y^3$ are independently C, O, N, NR$^2$ or S, wherein $R^2$ is H, substituted or unsubstituted $C_1$-$C_6$ alkyl, substituted or unsubstituted $C_2$-$C_6$ alkenyl, substituted or unsubstituted cycloalkyl, aryl or heteroaryl; and
$Y^2$ is C or N.

4. A compound according to claim 3, or a salt thereof, wherein:
$R^1$ is H, —Cl, —F, —Br, —I, —OH, —CN, —NO$_2$, or substituted or unsubstituted $C_1$-$C_6$ alkyl;
$R^3$ is —[(CH$_2$)$_2$E]$_n$(CH$_2$)$_2$NR'R" wherein n is any integer from 0 through 12, R' and R" are each independently H, substituted or unsubstituted $C_1$-$C_6$ alkyl, substituted or unsubstituted $C_2$-$C_6$ alkenyl, or substituted or unsubstituted cycloalkyl, and E is $CH_2$, O, NH or S, or E is absent;

$R^4$ is H, —Cl, —F, —Br, —I, —OH, —CN, —$NO_2$, or substituted or unsubstituted $C_1$-$C_6$ alkyl; and $Y^1$ and $Y^3$ are independently C, O, N, $NR^2$ or S, wherein $R^2$ is H, —$CH_3$, —$CH_2CH_3$, —$CH(CH_3)_2$, —$CH_2CH(CH_3)_2$, —$(CH)_mCH_3$ wherein m is 1, 2, 3, 4 or 5, or —$C(CH_3)_3$; and $Y^2$ is C.

5. A compound as shown below

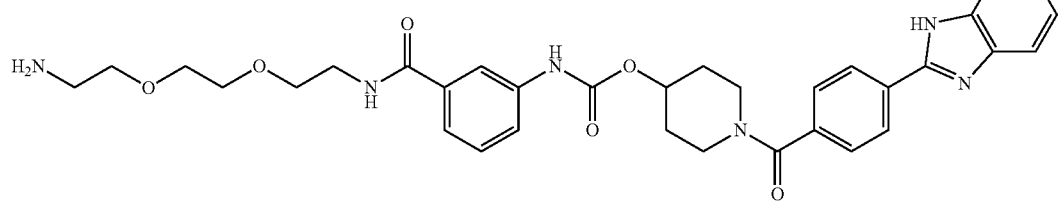

or a salt thereof.

6. A pharmaceutical composition comprising a therapeutic agent and a compound or salt thereof according to claim 1.

7. A method of extending the half life of a therapeutic agent comprising conjugating the agent to a compound or salt thereof according to claim 1 and administering it to a patient.

8. An affinity chromatography solid phase comprising a compound or salt thereof according to claim 1.

9. A pharmaceutical composition comprising a therapeutic agent and a compound or salt thereof according to claim 3.

10. A method of extending the half life of a therapeutic agent comprising conjugating the agent to a compound or salt thereof according to claim 3 and administering it to a patient.

11. An affinity chromatography solid phase comprising a compound or salt thereof according to claim 3.

12. A pharmaceutical composition comprising a therapeutic agent and a compound or salt thereof according to claim 5.

13. A method of extending the half life of a therapeutic agent comprising conjugating the agent to a compound or salt thereof according to claim 5 and administering it to a patient.

14. An affinity chromatography solid phase comprising a compound or salt thereof according to claim 5.

15. A compound according to claim 1, or a salt thereof, wherein:

$Y^1$ is O, $NR^2$ or S, wherein $R^2$ is H, substituted or unsubstituted $C_1$-$C_6$ alkyl, substituted or unsubstituted $C_2$-$C_6$ alkenyl, substituted or unsubstituted cycloalkyl, aryl or heteroaryl;

$Y^3$ is N; and $Y^2$ is C.

16. A compound according to claim 15, or a salt thereof, wherein $R^2$ is H or unsubstituted $C_1$-$C_6$ alkyl.

17. A compound according to claim 15, or a salt thereof, wherein:

A and D are independently

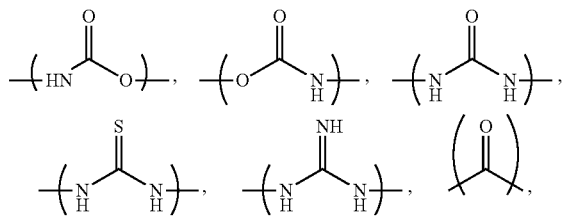

-continued

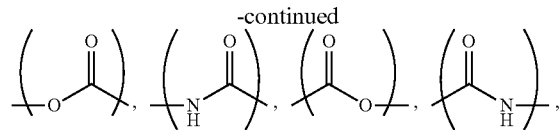

or A and/or D is absent.

18. A compound according to claim 2, or a salt thereof, wherein: $Y^1$ is O, $NR^2$ or S; and $Y^3$ is N.

19. A compound according to claim 18, wherein: $R^2$ is H, —$CH_3$, —$CH_2CH_3$, —$CH(CH_3)_2$, —$CH_2CH(CH_3)_2$, or —$C(CH_3)_3$.

20. A compound according to claim 18, wherein:

A and D are independently

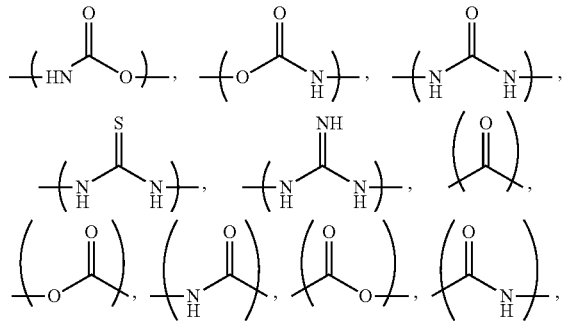

or A and/or D is absent.

21. A compound according to claim 1, or a salt thereof, wherein:

$R^1$ is H, —Cl, —F, —Br, or —I;

$R^3$ is —$[(CH_2)_2E]_n(CH_2)_2NR'R''$ wherein n is any integer from 0 through 30, R' and R" are each H, and E is $CH_2$, O, NH or S, or E is absent;

$R^4$ is H, —Cl, —F, —Br, or —I;

$Y^1$ and $Y3$ are independently C, O, N, $NR^2$ or S, wherein $R^2$ is H;

$Y^2$ is C or N;

A and D are independently

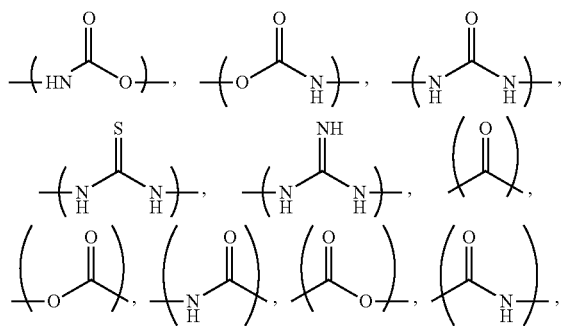

amidine, thioamide, or A and/or D is absent;
B is unsubstituted $C_4$-$C_9$-cycloalkyl, unsubstituted $C_4$-$C_9$-heterocycloalkyl comprising N, or unsubstituted heteroaryl comprising N, S or O, or B is absent; and
Z is substituted or unsubstituted aryl or unsubstituted heteroaryl comprising N, O or S, or Z is absent.

22. A compound according to claim 21, or a salt thereof, wherein:
$Y^1$ is O, $NR^2$ or S, wherein $R^2$ is H;
$Y^3$ is N; and
$Y^2$ is C.

23. A compound according to claim 22, or a salt thereof, wherein:
A and D are independently

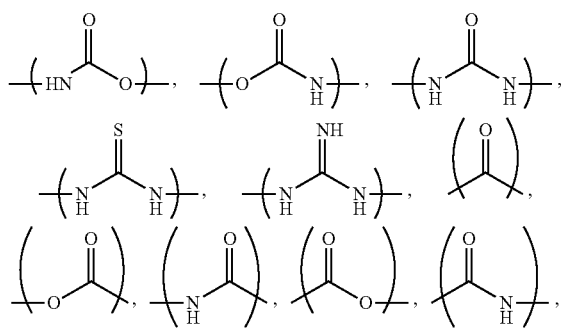

or A and/or D is absent.

24. A compound according to claim 1, or a salt thereof, wherein:
$R^1$ is H, —Cl, —F, —Br, —I, —OH, —CN, —NO$_2$, unsubstituted $C_1$-$C_6$ alkyl, unsubstituted $C_2$-$C_6$ alkenyl, unsubstituted cycloalkyl, aryl or heteroaryl;
$R^3$ is —[(CH$_2$)$_2$E]$_n$(CH$_2$)$_2$NR'R" wherein n is any integer from 0 through 30, R' and R" are each independently H, unsubstituted $C_1$-$C_6$ alkyl, unsubstituted $C_2$-$C_6$ alkenyl, or unsubstituted cycloalkyl, and E is CH$_2$, O, NH or S, or E is absent;
$R^4$ is H, —Cl, —F, —Br, —I, —OH, —CN, —NO$_2$, unsubstituted $C_1$-$C_6$ alkyl, unsubstituted $C_2$-$C_6$ alkenyl, unsubstituted cycloalkyl, aryl or heteroaryl;
$Y^1$ and $Y^3$ are independently C, O, N, $NR^2$ or S, wherein $R^2$ is H, unsubstituted $C_1$-$C_6$ alkyl, unsubstituted $C_2$-$C_6$ alkenyl, unsubstituted cycloalkyl, aryl or heteroaryl;
$Y^2$ is C or N;

A and D are independently

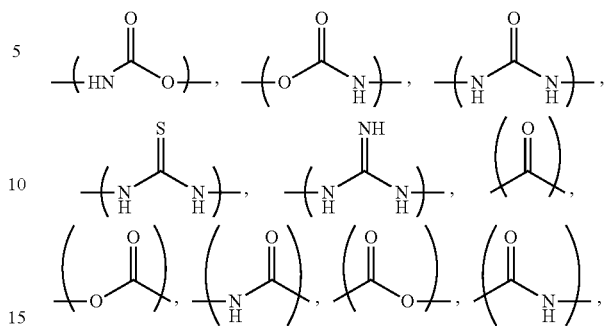

amidine, thioamide or A and/or D is absent;
B is unsubstituted $C_4$-$C_9$-cycloalkyl, unsubstituted $C_4$-$C_9$-heterocycloalkyl comprising N, unsubstituted heteroaryl comprising N, S or O, or B is absent; and
Z is unsubstituted aryl or unsubstituted heteroaryl comprising N, O or S, or Z is absent.

25. A compound according to claim 24, or a salt thereof, wherein:
$Y^1$ is O, $NR^2$ or S, wherein $R^2$ is H, unsubstituted $C_1$-$C_6$ alkyl, unsubstituted $C_2$-$C_6$ alkenyl, unsubstituted cycloalkyl, aryl or heteroaryl;
$Y^3$ is N; and
$Y^2$ is C.

26. A compound according to claim 25, or a salt thereof, wherein $R^2$ is H or unsubstituted $C_1$-$C_6$ alkyl.

27. A compound according to claim 25, or a salt thereof, wherein:
A and D are independently

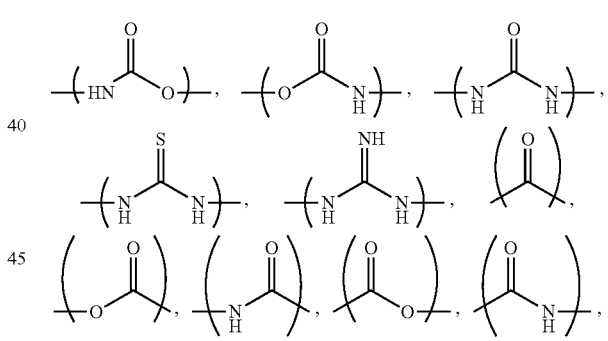

or A and/or D is absent.

28. A compound according to claim 3, or a salt thereof, wherein:
$Y^1$ is O, $NR^2$ or S, wherein $R^2$ is H, substituted or unsubstituted $C_1$-$C_6$ alkyl, substituted or unsubstituted $C_2$-$C_6$ alkenyl, substituted or unsubstituted cycloalkyl, aryl or heteroaryl;
$Y^3$ is N; and
$Y^2$ is C.

29. A compound according to claim 28, or a salt thereof, wherein: $R^2$ is H or unsubstituted $C_1$-$C_6$ alkyl.

30. A compound according to claim 3, or a salt thereof, wherein:
$R^1$ is H, —Cl, —F, —Br, or —I;
$R^3$ is —[(CH$_2$)$_2$E]$_n$(CH$_2$)$_2$NR'R" wherein n is any integer from 0 through 30, R' and R" are each H, and E is CH$_2$, O, NH or S, or E is absent;
$R^4$ is H, —Cl, —F, —Br, or —I;

$Y^1$ and $Y^3$ are independently C, O, N, $NR^2$ or S, wherein $R^2$ is H; and $Y^2$ is C or N.

31. A compound according to claim 30, or a salt thereof, wherein n is any integer from 0 through 12, and $Y^2$ is C.

32. A compound according to claim 4, or a salt thereof, wherein:

$Y^1$ is O, $NR^2$ or S, wherein $R^2$ is H, —$CH_3$, —$CH_2CH_3$, —$CH(CH_3)_2$, —$(CH)_2CH(CH_3)_2$, or $(CH)_mCH_3$ wherein m is 1, 2, 3, 4 or 5, or $C(CH_3)_3$; and $Y^3$ is N.

* * * * *